US009421284B2

(12) United States Patent
Sugita et al.

(10) Patent No.: US 9,421,284 B2
(45) Date of Patent: Aug. 23, 2016

(54) BIOMOLECULE LABELING REACTION CONTAINER, AND REACTOR AND REACTION METHOD USING THE SAME

(71) Applicant: Hitachi, Ltd., Tokyo (JP)

(72) Inventors: Nami Sugita, Tokyo (JP); Naomi Manri, Tokyo (JP); Wataru Takeuchi, Tokyo (JP); Yuichi Morimoto, Tokyo (JP); Hiroko Hanzawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/235,005

(22) PCT Filed: Dec. 26, 2012

(86) PCT No.: PCT/JP2012/083744

§ 371 (c)(1),
(2) Date: Jan. 24, 2014

(87) PCT Pub. No.: WO2014/102944

PCT Pub. Date: Jul. 3, 2014

(65) Prior Publication Data

US 2015/0335769 A1 Nov. 26, 2015

(51) Int. Cl.
*B01J 19/24* (2006.01)
*A61K 51/08* (2006.01)
(Continued)

(52) U.S. Cl.
CPC ........... *A61K 51/088* (2013.01); *B01F 13/0062* (2013.01); *B01F 13/0066* (2013.01);
(Continued)

(58) Field of Classification Search
CPC .... Y10T 436/12; Y10T 436/00; B01J 19/006; B01J 19/24; B01J 2219/00049; B01J 2219/00; B01J 2219/24
USPC ................ 436/55; 422/50, 63, 68.1, 500, 547
See application file for complete search history.

(56) References Cited

U.S. PATENT DOCUMENTS

2003/0162283 A1 8/2003 Kuno et al.
2008/0064110 A1 3/2008 Elizarov et al.

FOREIGN PATENT DOCUMENTS

JP 2003-315337 A 11/2003
JP 2007-136280 A 6/2007
(Continued)

OTHER PUBLICATIONS

Machine Translation of JP 2010-235462 A of Claims and Detailed Description, submitted on IDS on Jan. 24, 2014. obtained on Sep. 28, 2015 from Japant Platform fo rPatent Information, pp. 1-21.*
(Continued)

*Primary Examiner* — Christine T Mui
(74) *Attorney, Agent, or Firm* — Brundidge & Stanger, P.C.

(57) ABSTRACT

A reaction container in which to mix a first chemical compound with a second chemical compound has a main body and a lid member formed oppositely on a top face side of the main body; a flow channel on the top face of the main body; and a labeling agent solidification section at an intermediate section of the flow channel to remove a solvent in a solution of the second chemical compound and solidify the second chemical compound. First and second chemical compound supply sections and a mixture discharge section are formed on the upstream and downstream sides of the labeling agent solidification section, respectively. The reactor is provided with a liquid sending unit to supply the first and second chemical compounds and reciprocally send a solution of the first chemical compound to an upper part of the second chemical compound solidified at the solidification section.

9 Claims, 17 Drawing Sheets

(51) Int. Cl.
*B01J 19/00* (2006.01)
*B01L 3/00* (2006.01)
*B01F 13/00* (2006.01)
*C07B 59/00* (2006.01)

(52) U.S. Cl.
CPC ......... *B01J19/0006* (2013.01); *B01J 19/0093* (2013.01); *B01J 19/24* (2013.01); *B01L 3/5027* (2013.01); *B01L 3/502715* (2013.01); *B01J 2219/00049* (2013.01); *B01J 2219/0088* (2013.01); *B01J 2219/00783* (2013.01); *B01J 2219/00822* (2013.01); *B01J 2219/00828* (2013.01); *B01J 2219/00831* (2013.01); *B01J 2219/00833* (2013.01); *B01J 2219/00837* (2013.01); *B01J 2219/00842* (2013.01); *B01J 2219/00873* (2013.01); *B01J 2219/00889* (2013.01); *B01J 2219/00891* (2013.01); *B01J 2219/00905* (2013.01); *B01J 2219/00957* (2013.01); *B01J 2219/00961* (2013.01); *B01J 2219/00963* (2013.01); *B01J 2219/00986* (2013.01); *B01J 2219/24* (2013.01); *B01L 2300/069* (2013.01); *B01L 2300/0816* (2013.01); *B01L 2300/0887* (2013.01); *C07B 59/00* (2013.01); *Y10T 436/12* (2015.01)

(56) References Cited

FOREIGN PATENT DOCUMENTS

| | | |
|---|---|---|
| JP | 2008-128906 A | 6/2008 |
| JP | 2010-531295 A | 9/2010 |
| JP | 2010-235462 A | 10/2010 |
| WO | 2008/128201 A1 | 10/2008 |

OTHER PUBLICATIONS

Y. Murakami, H. Takamatsu, J. Taki, M. Tatsumi, A. Noda, R. Ichise, J. F. Tait, and S. Nishimura: "18F-1abelled annexin V: a PET tracer for apoptosis imaging": European Journal of Nuclear and Medicine Moleculur Imaging, vol. 31, No. 4, pp. 469-474, Apr. 2004.

P. Johnstrom, J. C. Clark, J. D. Pickard, A. P. Davenport: "Automated synthesis of the generic peptide labeling agent N-succinimidyl 4-[18F] fluorobenzoate and application to 18F-label the vasoactive transmitter urotensin-II as a ligand for positron emission tomography": Nuclear Medicine and Biology, 35, pp. 725-731 (2008).

M. Glaser, E. Arstand, S. K. Luthra, E. G. Robins: "Two-step radiosynthesis of [18F]N-succinimidyl-4-fluorobenzoate ([18F]SFB)": J. Label Compd. Radiopharm., 52, pp. 327-330 (2009).

W. Y. Tseng, J. S. Cho, X. Ma, A. Kunihiro, A. Chatziioannou, R. M. vanDam: "Toward Reliable Synthesis of Radiotracers for Positron Emission Tomography in PDMS Microfluidic Chips: Study and Optimization of the [18F] Fluoride Drying Process": Technical Proceedings of the 2010 NSTI Nanotechnology Conference & Expo-Nanotech 2010, vol. 2, 2010, pp. 472-475.

* cited by examiner

| SECTION | EXAMPLE 2 REACTION CONTAINER | | |
|---|---|---|---|
| | FLOW CHANNEL WIDTH (μm) | NUMBER OF FLOW CHANNELS (NUMBER) | CAPACITY (μm) |
| BIOMOLECULE SOLUTION INDUCTION FLOW CHANNEL SECTION | 200 | 31 | 7 |
| RADIOACTIVITY LABELING AGENT SOLIDIFICATION SECTION | — | — | 17 |
| DISCHARGE SIDE FLOW CHANNEL SECTION | 500 | 1 | 3 |
| TOTAL | — | — | 27 |

BIOMOLECULE LABELING REACTION CONTAINER, AND REACTOR AND REACTION METHOD USING THE SAME

TECHNICAL FIELD

The present invention relates to a reaction container used for labeling a biomolecule, and a reactor and a reaction method using the reaction container.

BACKGROUND ART

In diagnostic nuclear medicine, a radioactive pharmaceutical (a pharmaceutical containing a radioactive substance) is administered in a biological body and an image reflecting a vital function is obtained through PET (Positron Emission Tomography), a gamma camera, or the like.

As a radioactive pharmaceutical, a pharmaceutical obtained by labeling a biomolecule interacting with a disease-related substance with a radioactive substance is expected as a pharmaceutical to specifically detect a disease and the research and development of a novel pharmaceutical is actively worked on (refer to Non-Patent Literatures 1 and 2 for example).

It is desirable to perform a labeling reaction with a radioactive substance under a moderate condition in order to maintain the function of a biomolecule interacting with a disease-related substance. In the case of synthesizing an 18F labeling material that is a typical PET pharmaceutical for example, an 18F labeling process is usually carried out at a high temperature of around 100° C. (refer to Non-Patent Literature 3 for example). Since deactivation of a function in a biomolecule is concerned at a high temperature, however, a method of not applying labeling directly in the process but applying reaction with an 18F labeling agent labeled with 18F at around room temperature is the mainstream (refer to Non-Patent Literatures 1 and 2 for example).

Further, many of the 18F labeling agents are water-insoluble chemical compounds and a reaction solution is an organic solvent solution such as acetonitrile and ether that is concerned about the deactivation of the function of a biomolecule. To cope with that, a manufacturing method of introducing an 18F labeling agent into a reaction container, evaporating a solvent to dryness, thereafter adding a biomolecule aqueous solution, and leaving it at rest for a given length of time without applying agitation that is also concerned about the deactivation of the function of a biomolecule is adopted (refer to Non-Patent Literatures 1 and 2 for example).

PRIOR ART LITERATURE

Non-Patent Literature

Non-Patent Literature 1: Y. Murakami, H. Takamatsu, J. Taki, M. Tatsumi, A. Noda, R. Ichise, J. F. Tait, and S. Nishimura: 18F-labelled Annexin V: a PET Tracer for Apoptosis Imaging: Eur. J. Nucl. Med. Mol. Imaging, 31, 469 (2004)

Non-Patent Literature 2: P. Johnstrom, J. C. Clark, J. D. Pickard, A. P. Davenport: Automated synthesis of the generic peptide labeling agent N-Succinimidyl 4-[18F] fluorobenzoate and application to 18F-label the vasoactive transmitter urotensin-II as a Ligand for positron emission tomography: Nucl. Med. Biol., 35, 725 (2008)

Non-Patent Literature 3: M. Glaser, E. Arstand, S. K. Luthra, E. G. Robins: Two-stepradiosynthesis of [18F]N-Succinimidyl 4-[18F] fluorobenzoate ([18F]SFB): J. Label Compd. Radiopham., 52, 327 (2009)

SUMMARY OF INVENTION

Problem to be Solved by the Invention

As stated above, in the manufacturing methods in Non-Patent Literatures 1 and 2, there is a high possibility of being able to maintain the function of a biomolecule because an organic solvent is not used and a reaction solution is not agitated at room temperature, but a problem is that an 18F labeling agent is a water-insoluble chemical compound and hence is hardly soluble in water and the reaction progresses slowly.

The radioactivity of a radioactive pharmaceutical has a half-life. In particular, the half-life of the nuclide of a PET pharmaceutical is as short as 20 min. in the case of 11C and 110 min. in the case of 18F. When reaction progresses slowly as stated above, although it is possible to improve the yield of an objective substance by prolonging reaction time in an ordinary chemical reaction, a problem is that the radioactivity decays and a radiochemical yield deteriorates when the reaction time is prolonged in the reaction of a radioactive pharmaceutical.

In view of the above situation, an object of the present invention is to provide: a reaction container that allows the progression of reaction to be accelerated and reaction time considering the decay of radioactivity to be selected even under a moderate condition of maintaining the function of a biomolecule; and a reactor and a reaction method using the reaction container.

Means for Solving the Problem

In order to solve the above problems, the present invention includes several means for solving the problems and an example of a biomolecule labeling reaction container according to the present invention is a reaction container to mix a first chemical compound that is a biomolecule with a second chemical compound that is a labeling agent, wherein: the reaction container has a reaction container main body and a lid member formed oppositely on a top face side of the reaction container main body; the reaction container has introduction sections of the first chemical compound and the second chemical compound and a recovery section of a mixture on a bottom face side of the reaction container main body; a flow channel is formed on the top face of the reaction container main body; a labeling agent solidification section to remove a solvent in the solution of the second chemical compound and solidify the second chemical compound is formed at an intermediate section of the flow channel; and, in the flow channel, a supply section of the first chemical compound and a supply section of the second chemical compound are formed on the upstream side of the labeling agent solidification section and a discharge section of the mixture is formed on the downstream side of the labeling agent solidification section.

In a biomolecule labeling reaction container according to the present invention, it is desirable that the labeling agent is a radioactivity labeling agent and that the biomolecule labeling reaction container has a radiation sensor.

Further, an example of a reactor according to the present invention is a reactor to mix a first chemical compound that is a biomolecule with a second chemical compound that is a labeling agent in a reaction container, including: a reaction container unit including a reaction container wherein a flow channel is formed on a top face of a reaction container main body, a labeling agent solidification section to remove a solvent in the solution of the second chemical compound and solidify the second chemical compound is formed at an intermediate section of the flow channel, a supply section of the first chemical compound and a supply section of the second chemical compound are formed on the upstream side of the labeling agent solidification section, and a discharge section of the mixture is formed on the downstream side of the labeling agent solidification section; a liquid sending unit to supply the first chemical compound and the second chemical compound to the reaction container respectively and reciprocally send a solution of the first chemical compound to an upper part of the second chemical compound solidified at the labeling agent solidification section; a recovery unit to recover a mixed solution mixed in the reaction container; and a control unit to control the reaction container unit, the liquid sending unit, and the recovery unit.

Furthermore, an example of a reaction method according to the present invention is a reaction method of mixing a first chemical compound that is a biomolecule with a second chemical compound that is a labeling agent by using a reaction container wherein a flow channel is formed on a top face of a reaction container main body, a labeling agent solidification section is formed at an intermediate section of the flow channel, a supply section of the first chemical compound and a supply section of the second chemical compound are formed on the upstream side of the labeling agent solidification section, and a discharge section of the mixture is formed on the downstream side of the labeling agent solidification section, the method including the processes of: introducing a solution of the second chemical compound that is the labeling agent from a supply section of the second chemical compound into the labeling agent solidification section, removing a solvent, and solidifying the second chemical compound; introducing a solution of the first chemical compound that is the biomolecule from a supply section of the first chemical compound; and allowing a solution of the first chemical compound to pass reciprocally through an upper part of the solidified second chemical compound and mixing the first chemical compound with the second chemical compound.

Effect of the Invention

The present invention makes it possible to accelerate the progression of reaction even under a moderate condition of maintaining the function of a biomolecule and to select reaction time considering the decay of radioactivity.

Problems, configurations, and effects other than above will be obvious from the explanations in the following embodiments.

MODE FOR CARRYING OUT THE INVENTION

Embodiments according to the present invention are explained hereunder in reference to drawings. Here, the embodiments according to the present invention are not limited to examples mentioned hereafter and various modifications within the scope of the technological thought are included in the present invention. Here, in all the drawings explaining the embodiments, members having the same functions are represented by the same or related symbols and repetitive explanations are avoided. Further, in the following embodiments, explanations on the same or similar parts are not repeated in principle unless otherwise needed.

The present invention is explained hereunder by dividing it into plural sections or plural embodiments but, unless otherwise specified, they are not unrelated to each other and one is in the relationship with a modified example, an applied example, a detailed explanation, a supplemental explanation, or the like of the all or a part of another. Further, in the following embodiments, when the number of elements and others (including the number of pieces, a numerical value, a quantity, a range, and others) are referred to, the number is not limited to the specific number and may be a number smaller or larger than the specific number unless specified specifically or specified obviously in principle to the specific number.

In the following embodiments, a constituent component thereof (including an element step and others) is not necessarily essential except the case of being specified specifically or being considered obviously as essential in principle. Likewise, in the following embodiments, when a shape, positional relationship, and others of a constituent component and others are referred to, a shape close or similar to the shape is substantially included in the shape except the case of being specified specifically or being considered obviously as otherwise in principle. The same shall apply to the aforementioned number and others (including the number of pieces, a numerical value, a quantity, a range, and others).

[Device Configuration]

[Overall Configuration]

Figure 1:
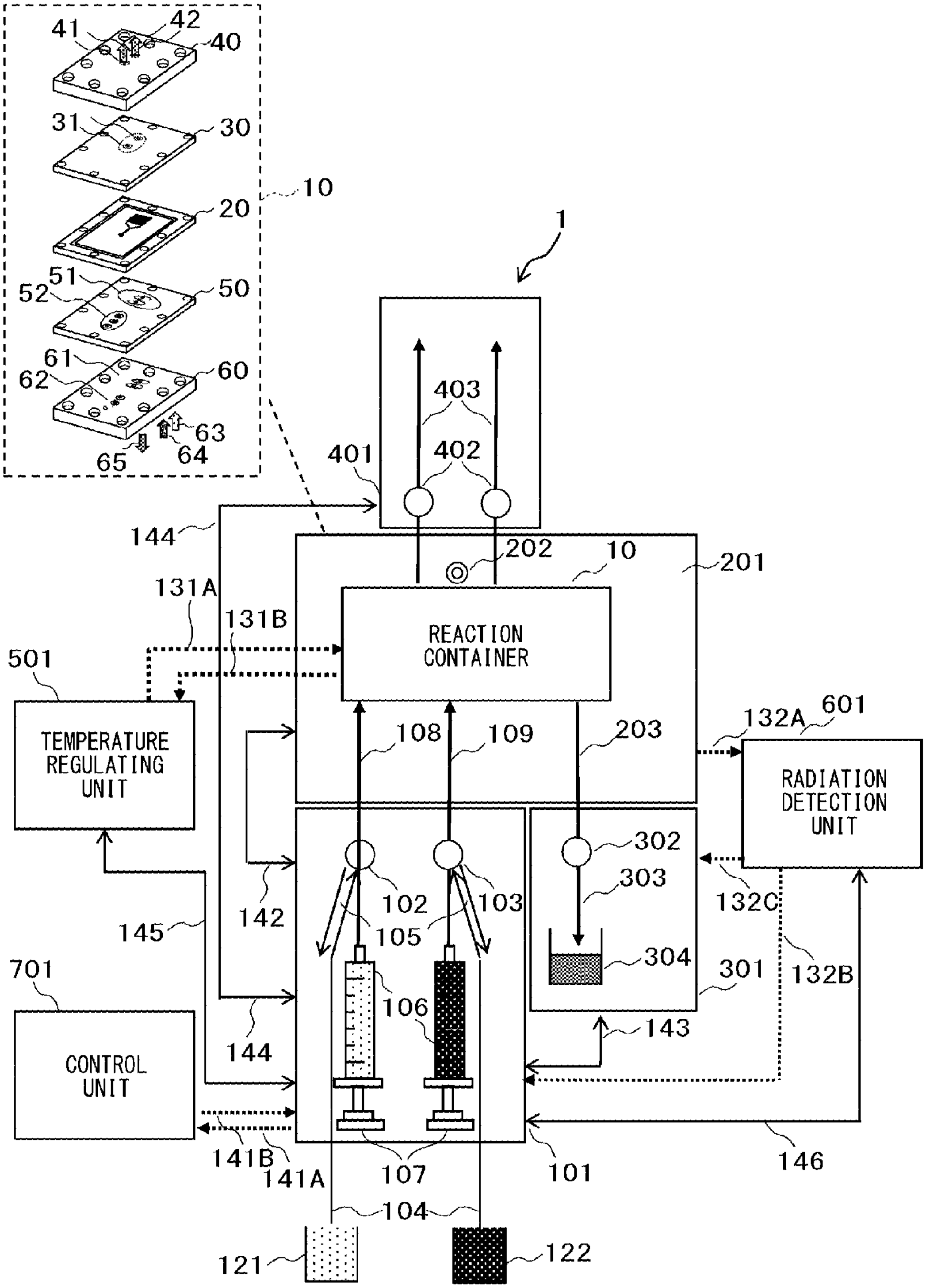
FIG. 1 is a view showing an example of a biomolecule radioactivity labeling reactor according to the present invention.

Explanations are made on the basis of the case of applying a reaction container according to the present invention to biomolecule radioactivity labeling reaction. FIG. 1 is an example of a biomolecule radioactivity labeling reactor using a biomolecule radioactivity labeling reaction container and a radioactive biomolecule pharmaceutical is manufactured with the reactor. It is a matter of course that the application of the present invention is not limited to the manufacturing of a radioactive biomolecule pharmaceutical.

A biomolecule radioactivity labeling reactor 1 shown in FIG. 1 includes a liquid sending unit 101, a reaction container unit 201, a recovery unit 301, an exhaust unit 401, a temperature regulating unit 501, a radiation detection unit 601, and a control unit 701.

The liquid sending unit 101 is a unit used for sending a biomolecule solution 121, a radioactivity labeling agent solution 122, and a mixture solution 304.

The reaction container unit 201 is a unit having a biomolecule radioactivity labeling reaction container 10 and is used for producing a radioactive biomolecule pharmaceutical by reacting the biomolecule solution 121 and the radioactivity labeling agent solution 122. Here, the biomolecule radioactivity labeling reaction container 10 corresponds to a reaction container in the present invention.

The recovery unit 301 is a unit used for recovering the solution (mixture solution) 304 mixed in the biomolecule radioactivity labeling reaction container 10. The exhaust unit 401 is a unit to evaporate and exhaust a solvent of the radioactivity labeling agent solution 122 introduced into the biomolecule radioactivity labeling reaction container 10. The temperature regulating unit 501 is a unit to control the temperature of the biomolecule radioactivity labeling reaction container 10. The radiation detection unit 601 is a unit to detect a radiation quantity of the reaction container unit 201. The control unit 701 is a unit to control the liquid sending unit 101, the reaction container unit 201, the recovery unit 301, the exhaust unit 401, the temperature regulating unit 501, and the radiation detection unit 601. The control unit 701 includes a computer for example.

[Detailed Structure of Units]

The liquid sending unit 101 has (1) liquid sending switch valves 102 and 103 to switch the operations of solution sucking, liquid sending, liquid wasting, and closing, (2) solution sucking lines 104, (3) solution wasting lines 105, (4) syringes 106, (5) syringe pumps 107, (6) a biomolecule solution introduction section 108, and (7) a radioactivity labeling agent solution introduction section 109 in the interior. The liquid sending unit 101 further includes devices not shown in the figure, such as (1) a pressure sensor to monitor pressure in the system, (2) holders to fix the syringes, (3) an electric power switch, (4) an emergency stop switch in the case of abnormal action, (5) a connector for communication, (6) a sample loop to introduce a small quantity of raw material, (7) fittings to connect lines and sample loops to the switch valves 102 and 103, and others.

The reaction container unit 201 includes (1) the biomolecule radioactivity labeling reaction container 10, (2) a radiation sensor 202, and (3) a reservoir section 203. Here, fittings not shown in the figure are used for connecting the biomolecule radioactivity labeling reaction container 10 to the biomolecule solution introduction section 108, the radioactivity labeling agent solution introduction section 109, and the reservoir section 203, respectively.

The recovery unit 301 includes (1) a recovery switch valve 302 for switching liquid sending and closing operations and (2) a mixture solution recovery line 303. Here, fittings not shown in the figure are used for connecting the recovery switch valve 302 to the reservoir section 203 and the mixture solution recovery line 303, respectively.

The exhaust unit 401 includes (1) exhausting switch valves 402 for switching exhausting, air supplying, and closing operations and (2) exhausting lines 403. Here, fittings not shown in the figure are used for connecting the exhausting switch valves 402 to the exhausting lines 403, respectively.

The temperature regulating unit 501 transmits and receives a temperature control signal 131A and a feedback signal 131B to and from the reaction container unit 201. It is possible to control the temperature of the biomolecule radioactivity labeling reaction container 10 by transmitting and receiving those signals. As methods for regulating the temperature of the biomolecule radioactivity labeling reaction container 10, there are: a method of circulating a heat medium by using a circulation and constant-temperature bath; and methods of using a Peltier element, a ribbon heater, and a plate-type heater for example. Further, as temperature-controlled objects, a heat medium circulating around the biomolecule radioactivity labeling reaction container 10 and the outside and the interior of the biomolecule radioactivity labeling reaction container 10 are named for example. For example, more accurate temperature control can materialize by using a solution flowing inside the biomolecule radioactivity labeling reaction container 10, a solution introduced inside it, or a site near the solution flowing inside it as the controlled object.

The radiation detection unit 601 receives a radiation detection signal 132A from the reaction container unit 201 and transmits feedback signals 132B and 132C to the liquid sending unit 101 and the recovery unit 301. The radiation detection unit 601: judges the progress of radioactivity labeling reaction by the value of a detected radiation quantity given from the radiation sensor 202 as the radiation detection signal 132A and; on the basis of the judgment result, outputs the feedback signal 132B for switching the liquid sucking and sending of the liquid sending switch valve 102 and the feedback signal 132C for switching the closing and recovery of the recovery switch valve 302. It is possible to recover an objective substance by the switching while the progress of the reaction is assessed. The radiation sensor 202 in the reaction container unit 201 is installed close to the flow channel in the biomolecule radioactivity labeling reaction container 10 to the greatest possible extent of detecting an intended radiation. Further, unintended radiation is shielded in the range of allowing the intended radiation to be detected. More accurate radiation detection materializes by the configuration.

The control unit 701 monitors and controls the operations of the aforementioned six units. For example, the control unit 701 transmits and receives a control signal 141A and a feedback signal 141B to and from the liquid sending unit 101 and monitors and controls operations in the liquid sending unit 101. Here, the liquid sending unit 101 relays communication between the control unit 701 and the other five units. To that end, a data communication signal 142 is transmitted and received between the liquid sending unit 101 and the reaction container unit 201, a data communication signal 143 is transmitted and received between the liquid sending unit 101 and the recovery unit 301, a data communication signal 144 is transmitted and received between the liquid sending unit 101 and the exhaust unit 401, a data communication signal 145 is transmitted and received between the liquid sending unit 101 and the temperature regulating unit 501, and a data communication signal 146 is transmitted and received between the liquid sending unit 101 and the radiation detection unit 601. The control unit 701 monitors and controls the reaction container unit 201, the recovery unit 301, the exhaust unit 401, the temperature regulating unit 501, and the radiation detection unit 601 through those data communication signals.

Specifically, the control unit 701 controls: the switching of the switch valves 102 and 103 in the liquid sending unit 101; the sucking and sending of a solution in the syringes 106 by the drive control of the syringe pumps 107; and the discarding of a solution filled in the syringes 106 to a waste tank or the like not shown in the figure. Further, the control unit 701 also controls halfway stoppage and restart in liquid sending control and sucking control.

By using the control unit 701, it is possible to set the sizes of the syringes 106, the quantities of sucked solutions and the sucking rates of the solutions sucked from the solution sucking lines 104, the quantities of sent solutions and the sending rates of the solutions sent to the reaction container unit 201, the quantities of sent solutions and the sending rates of the solutions sent to the solution wasting lines 105, reciprocal sending of a solution in the biomolecule radioactivity labeling reaction container 10, the temperature of the biomolecule radioactivity labeling reaction container 10, namely a solvent removal temperature and a reaction temperature. Further, it is also possible to set a "time-delay" of liquid sending and change liquid sending time for each of the syringes 106.

Further, by preparing beforehand an input file to indicate two or more operations to be consecutively performed in relation to the operations of the syringes 106 and valves accompanying liquid sucking and sending processes and reading the input file into the control unit 701, it is possible to automatically control a series of operations. By installing the automatic control function, it is possible to avoid radiation exposure and carry out remote automatic operation. Further, by storing the input file in a storage region in the control unit 701, reading the input file if needed, and thus activating it, it is also possible to rewrite the input file arbitrarily.

Further, the control unit 701 can record in the interior: pressure data in the system obtained from a pressure sensor, not shown in the figure, installed in the liquid sending unit 101; temperature information obtained from the temperature regulating unit 501; a detected value of radiation and time data obtained from the radiation detection unit 601; and others in the storage region. Furthermore, the control unit 701 can apply emergency stop to the whole device when a pressure in the system exceeds a threshold value by deciding the threshold value of the pressure in the system beforehand on the basis of the pressure resistance information of a pressure sensor and switch valves.

Here, as the materials of the solution sucking lines 104, the solution wasting lines 105, the biomolecule solution introduction section 108, the radioactivity labeling agent solution introduction section 109, the reservoir section 203, the mixture solution recovery line 303, the biomolecule radioactivity labeling reaction container 10, and others, any materials can be used as long as they are materials not adversely affecting reactions to be implemented and not adsorbing a material in the sent solutions and the materials can arbitrarily be changed in accordance with the temperatures, concentrations, and physical properties of the solutions flowing in the interior. As the materials, tungsten, stainless steel, silicon, glass, Hastelloy, silicon resin, fluorine resin, and others are named for example. Further, as the materials, materials produced by applying the coating of nickel or gold to the surface of glass lining, stainless steel, or silicon, materials produced by oxidizing the surface of silicon, and others, namely materials having improved corrosion resistance and materials having low adsorbability, can be used.

EXAMPLE 1

The structure of a biomolecule radioactivity labeling reaction container 10 is hereunder explained in detail. A development perspective view of a biomolecule radioactivity labeling reaction container 10 according to Example 1 is shown in FIG. 2.

Figure 2:
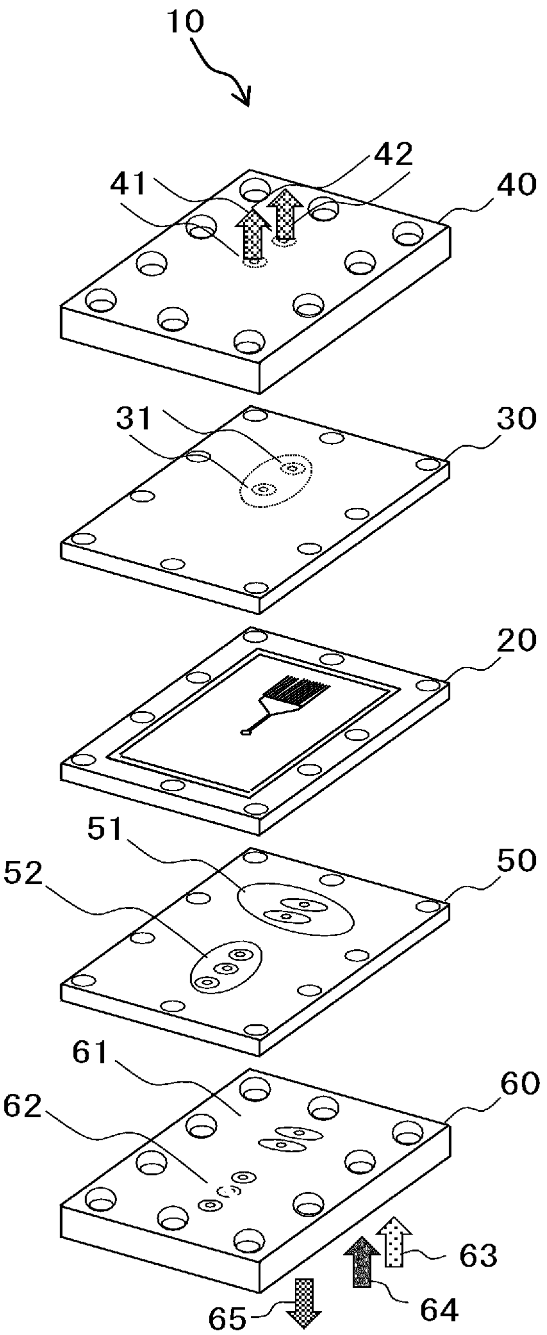
FIG. 2 is a development perspective view of a biomolecule radioactivity labeling reaction container according to Example 1 of the present invention.

As shown in FIG. 2, the biomolecule radioactivity labeling reaction container 10 has a reaction container main body 20 including a PEEK plate having a thickness of several millimeters, a lid member 30 including a PEEK plate and being placed on the upper face side of the reaction container main body 20, a lid member 40 including a SUS 316 stainless steel plate and being placed on the upper face side of the lid member 30, an adapter member 50 including a PEEK plate and being placed on the lower face side of the reaction container main body 20, and an adapter member 60 including a SUS 316 stainless steel plate and being placed on the lower face side of the adapter member 50.

The biomolecule radioactivity labeling reaction container 10 is configured by stacking the adapter member 60, the adapter member 50, the reaction container main body 20, the lid member 30, and the lid member 40 and fastening the peripheries of them with screws not shown in the figure.

Here, the lid member 30 constitutes a ceiling section of a flow channel formed in the manner of opening upward on the top face (upper face in the figure) side of the reaction container main body 20. Discharge outlet port sections 31 to evaporate and exhaust a solvent from the reaction container main body 20 are formed on the face (lower face in the figure) of the lid member 30 facing the reaction container main body 20 and communicate with the upper side face of the lid member 30 respectively.

Outlet sections 41 to evaporate and exhaust a solvent from the reaction container main body 20 are formed on the face (lower face in the figure) of the lid member 40 facing the lid member 30. The outlet sections 41 communicate with gas discharge ports 42 formed on the top face (upper face in the figure) of the lid member 40.

An inlet port section 51 to introduce a biomolecule solution and a radioactivity labeling solution into the reaction container main body 20 and an outlet port section 52 to discharge a mixture solution are formed on the face (upper face in the figure) of the adapter member 50 facing the reaction container main body 20 and communicate with the lower side face of the adapter member 50 respectively.

An inlet section 61 to introduce a biomolecule solution and a radioactivity labeling solution into the reaction container main body 20 and an outlet section 62 to discharge a mixture solution are formed on the face (upper face in the figure) of the adapter member 60 facing the adapter member 50. The inlet section 61 communicates with a biomolecule solution introduction port 63 and a radioactivity labeling agent solution introduction port 64, both of which are formed on the bottom face (lower face in the figure) of the adapter member 60. The outlet section 62 communicates with a mixture solution discharge port 65 formed on the bottom face (lower face in the figure) of the adapter member 60.

Sealing members including O-rings or the like made of fluoro-rubber not shown in the figure are installed at the periphery of the flow channel and others formed in the reaction container main body 20, the periphery of the discharge outlet port sections 31 formed in the lid member 30, and the peripheries of the inlet port section 51 and the outlet port section 52 formed in the adapter member 50.

Although the discharge outlet port sections 31 are formed in the lid member 30 and the outlet sections 41 are formed in the lid member 40 in order to evaporate and exhaust a solvent from the reaction container main body 20 in the present example, it is also possible not to form them but to use the outlet port section 52 formed in the adapter member 50 and the outlet section 62 and the mixture solution discharge port 65 formed in the adapter member 60.

The lid member 30 and the lid member 40 including different materials and the adapter member 50 and the adapter member 60 including different materials are installed respectively in the case of the present example. The purpose is to stably maintain the flow channel formed in the reaction container main body 20 and the reason is that the difference in hardness between the SUS 316 stainless steel plate and the PEEK plate forming the reaction container main body 20 is taken into consideration.

To that end, the lid member 30 including the same PEEK material as the reaction container main body 20 is installed between the lid member 40 including the SUS 316 stainless steel plate and the reaction container main body 20 and the adapter member 50 including the same PEEK material as the reaction container main body 20 is installed between the adapter member 60 and the reaction container main body 20.

When the reaction container main body 20 includes a material having hardness close to the SUS 316 stainless steel plate, the lid members 30 and 40 may be a single member including a SUS 316 stainless steel plate and the adapter members 50 and 60 may be a single member including a SUS 316 stainless steel plate.

Although the lid member 40 and the adapter member 60 include the SUS 316 stainless steel plates in the present example, they may also include a material capable of shielding the radiation of a radioactivity labeling agent introduced into the reaction container main body 20. As such materials, tungsten, lead, a workpiece for shielding, and others are named. When such a material for shielding radiation is used, it is necessary to form a space for detecting the radiation at either the lid member 40 or the adapter member 60.

Although the reaction container main body 20 includes a PEEK plate in the present example, it may include any material as long as the material does not adversely affect reaction occurring in the reaction container main body 20 and does not adsorb a substance in a solution introduced into the reaction container main body 20 and the material can arbitrarily be changed in accordance with the type of the reaction. As such materials, stainless steel, silicon, gold, glass, Hastelloy, silicon resin, fluorine resin can be named for example. Further, it is also possible to use materials produced by applying the coating of nickel or gold to the surface of glass lining or a metal, materials produced by oxidizing the surface of silicon, and others, namely materials having improved corrosion resistance and materials having low adsorbability.

The material of the sealing members stated above (not shown in the figure) may also be any material as long as it does not adversely affect reaction and the material can arbitrarily be changed in accordance with the type of performed reaction. Silicon resin or fluorine resin can be used for example.

A decomposable prefabricated unit using fluoro-rubber for the sealing members is adopted in the present example. A decomposable reaction container has high maintainability because the reaction container can be decomposed and cleaned when clogging or the like is caused in the interior. In FIG. 2, ten holes or tapped holes are formed at the peripheries of the adapter member 60, the adapter member 50, the reaction container main body 20, the lid member 30, and the lid member 40 and thus screw fastening is facilitated. Here, it is also possible to form an indecomposable reaction container by directly fixing the lid member 30 and the adapter member 50 to the top and bottom of the reaction container main body 20 by another method such as laser junction or an adhesive. An indecomposable reaction container makes it possible to avoid the leakage of an introduced solution and the like caused by poor sealing caused by the breakage of an O-ring. Further, it is possible to secure the quality of a pharmaceutical by making a reaction container disposable when it is used for reaction to manufacture the pharmaceutical applied to a bed-side.

Figure 3A:
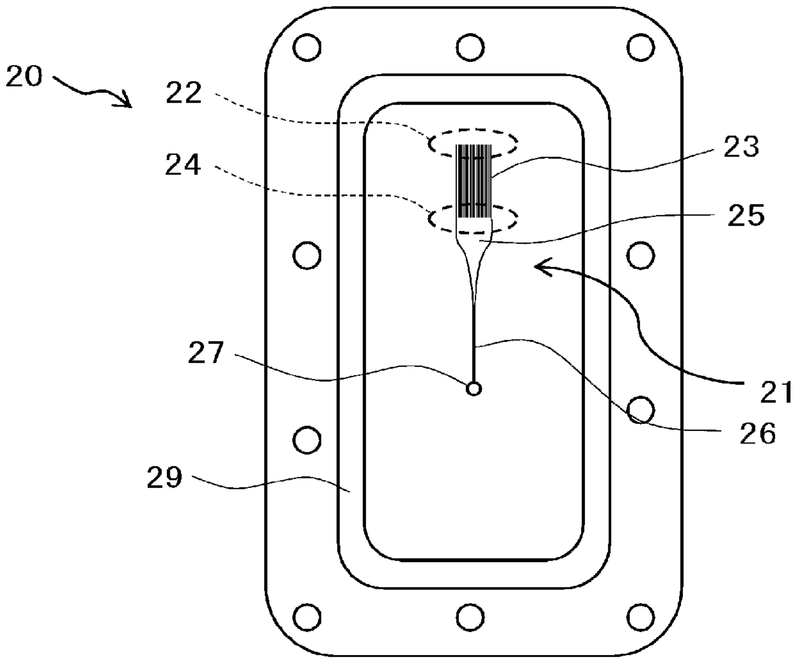
FIG. 3A is a front view explaining the structure of a reaction container main body according to Example 1 of the present invention.
Figure 3B:
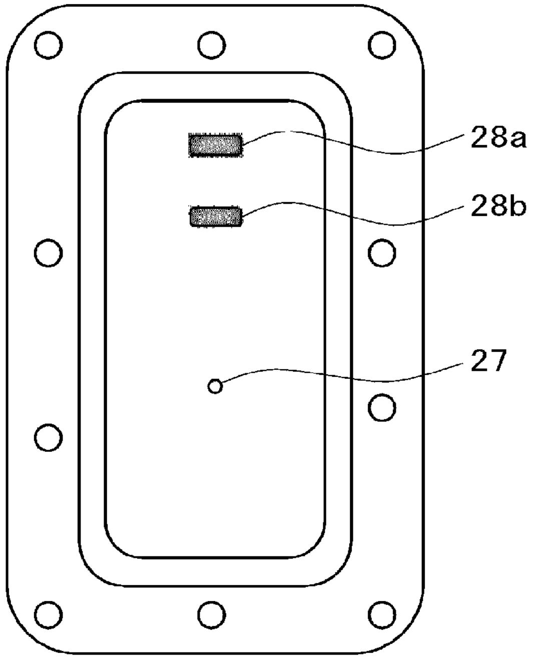
FIG. 3B is a rear view explaining the structure of a reaction container main body according to Example 1 of the present invention.
Figure 4:
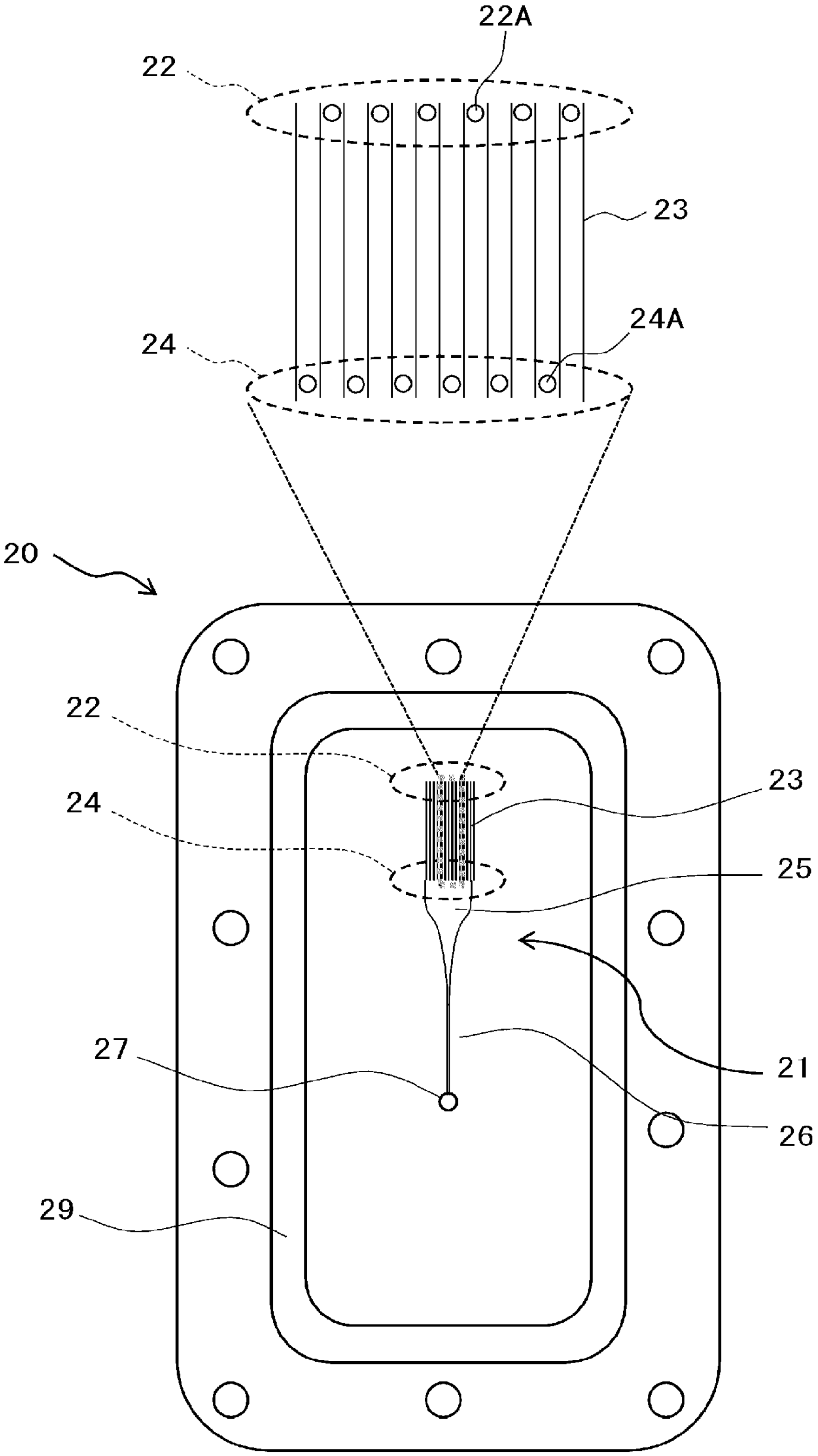
FIG. 4 is a partially enlarged view explaining a flow channel structure formed in a reaction container main body according to Example 1 of the present invention.

A front view and a rear view of a reaction container main body 20 constituting a biomolecule radioactivity labeling reaction container 10 are shown in FIGS. 3A and 3B. A partially enlarged view of a liquid sending structure formed in the reaction container main body 20 is shown in FIG. 4.

As shown in FIGS. 3A and 3B, four untapped holes for fastening are formed in the vertical direction and three untapped holes for fastening are formed in the lateral direction at the periphery of the reaction container main body 20. A rectangular groove 29 having round corners is formed on the side closer to the center than the holes. A sealing member not shown in the figures is attached to the groove 29.

A flow channel 21 to remove a solvent and mix a solidified radioactivity labeling agent with a biomolecule solution is formed on the side closer to the center than the groove 29 on the top face side of the reaction container main body 20 shown in FIG. 3A. A partially enlarged view of the flow channel is shown in FIG. 4.

The flow channel 21 according to the present example includes, from the upstream side in sequence, a biomolecule solution supply section 22, a biomolecule solution induction flow channel section 23, a radioactivity labeling agent solution supply section 24, a funnel-shaped radioactivity labeling agent solidification section 25, a discharge side flow channel section 26, and a mixed solution discharge section 27.

The biomolecule solution induction flow channel section 23 is configured as an assembly of thirty-one flow channels (first flow channels) each of which has a given width and is formed apart from another at a given distance in the width direction. Each of the flow channels constituting the biomolecule solution induction flow channel section 23 is configured as a space interposed by two walls formed in parallel. Both the ends of each of the thirty-one flow channels include open ends. The biomolecule solution supply section 22 to introduce a biomolecule solution 121 from the bottom face side of the reaction container main body 20 is formed at the uppermost stream section of the thirty-one flow channels. The biomolecule solution 121 introduced from the biomolecule solution supply section 22 is induced as a strip-shaped flow to an outlet port located on the lower end side in the figure. The outlet port of the biomolecule solution induction flow channel section 23 is connected to an inlet port side opening of the radioactivity labeling agent solidification section 25.

Here, the biomolecule solution supply section 22 includes thirty-one openings (biomolecule solution supply nozzles 22A) connecting the top face to the bottom face of the reaction container main body 20. As shown in FIG. 4, the biomolecule solution supply nozzles 22A are formed in a row at intervals nearly identical to the surface diameter of the nozzles in the direction of the width of the reaction container main body 20. The biomolecule solution 121 is introduced into the biomolecule solution induction flow channel section 23 through the biomolecule solution supply nozzles 22A.

Here, as shown in FIG. 3B, a biomolecule solution accumulation section 28*a* to temporarily accumulate the biomolecule solution 121 that is a supply liquid is formed on the bottom face of the reaction container main body 20 and the openings of the biomolecule solution supply nozzles 22A on the bottom face side are located in the region of the biomolecule solution accumulation section 28*a*. Incidentally, the biomolecule solution accumulation section 28*a* includes a recess sagging from the bottom face of the reaction container main body 20 in the thickness direction. The biomolecule solution accumulation section 28*a* is connected to an inlet port section 51 of an adapter member 50.

The radioactivity labeling agent solution supply section 24 is placed in spaces interposed by the thirty-one flow channels constituting the biomolecule solution induction flow channel section 23 and is used for introducing a radioactivity labeling agent solution 122 into the radioactivity labeling agent solidification section 25. As shown in FIG. 4, when the biomolecule solution induction flow channel section 23 includes the thirty-one parallel flow channels, thirty flow channels (second flow channels) having the same width as the biomolecule solution induction flow channel section 23 and being apart from each other at a given distance in the width direction are formed between the flow channels respectively. In the present example, the radioactivity labeling agent solution supply section 24 is placed at a most downstream position of the thirty flow channels.

The outlet ports of the second flow channels at which the radioactivity labeling agent solution supply section 24 is placed are connected to the inlet port side opening of the radioactivity labeling agent solidification section 25. Here, the radioactivity labeling agent solution supply section 24 includes thirty openings (radioactivity labeling agent solution supply nozzles 24A) connecting the top face to the bottom face of the reaction container main body 20. As shown in FIG. 4, the radioactivity labeling agent solution supply nozzles 24A are formed in a row at intervals nearly identical to the surface diameter of the nozzles in the direction of the width of the reaction container main body 20. The radioactivity labeling agent solution 122 is introduced into the radioactivity labeling agent solidification section 25 through the radioactivity labeling agent solution supply nozzles 24A.

Here, as shown in FIG. 3B, a radioactivity labeling agent solution accumulation section 28*b* to temporarily accumulate the radioactivity labeling agent solution 122 that is a supply liquid is formed on the bottom face of the reaction container main body 20 and the openings of the radioactivity labeling agent solution supply nozzles 24A on the bottom face side are located in the region of the radioactivity labeling agent solution accumulation section 28*b*. Incidentally, the radioactivity labeling agent solution accumulation section 28*b* includes a recess sagging from the bottom face of the reaction container main body 20 in the thickness direction. The radioactivity labeling agent solution accumulation section 28*b* is connected to the inlet port section 51 of the adapter member 50.

The radioactivity labeling agent solidification section 25 includes a recess sagging from the top face of the reaction container main body 20 in the thickness direction. The bottom face is formed so as to be lower than the biomolecule solution induction flow channel section 23. It is thereby possible to reserve the introduced radioactivity labeling agent solution 122 during the process of removing a solvent and solidifying it. Here, as shown in FIG. 2, discharge outlet port sections 31 are formed on the face of a lid member 30 facing the reaction container main body 20 at locations distant from the inflow side and the outflow side of the radioactivity labeling agent solidification section 25 to the extent that a radioactivity labeling agent solution does not flow out when the solvent of the radioactivity labeling agent solution 122 is evaporated and removed. Further, the discharge outlet port sections 31 are connected to outlet sections 41 of a lid member 40. The solvent of the radioactivity labeling agent solution 122 introduced into the radioactivity labeling agent solidification section 25 of the reaction container main body 20 is thereby discharged from gas discharge ports 42 formed on the top face (upper face in the figure) side of the lid member 40. The bottom face of the radioactivity labeling agent solidification section 25 has a depth of the extent that the radioactivity labeling agent solution 122 does not flow out from the discharge outlet port sections 31 of the lid member 30. It is also possible to install a filter not allowing a liquid to pass through on the side of the discharge outlet port sections 31 facing the reaction container main body 20 but allowing only a gas to pass through. By the filter, it is possible to prevent a solution from flowing out even when the radioactivity labeling agent solution 122 reaches the discharge outlet port sections 31.

Further, the radioactivity labeling agent solidification section 25 is manufactured in a funnel shape so that the width of the flow channel on the inflow side may be widest and the flow channel width may reduce toward the outflow side. The outlet port of the radioactivity labeling agent solidification section 25 is connected to the discharge side flow channel section 26 having a given length and a flow channel width identical to the port width. In the case of FIG. 4 therefore, it is possible to introduce a multi-layer flow including thirty-one strip-shaped flows introduced into the radioactivity labeling agent solidification section 25 into the discharge side flow channel section 26 in the state of shrinking in the width direction. That is, even when the flow channel width of the discharge side flow channel section 26 is thick to some extent, it is possible to narrow the width of the multi-layer flow formed inside. In this way, by introducing the biomolecule solution 121 passing through the solidified radioactivity labeling agent as a multi-layer flow into the discharge side flow channel section 26, it is possible to obtain stable mixing while the quantity of the sent liquid is secured.

Further, a mixture solution the reaction of which has progressed in the flow channel 21 is introduced into the mixture solution discharge section 27. The mixed solution discharge section 27 includes a hole connecting the top face to the bottom face of the reaction container main body 20 as shown in FIGS. 3A and 3B. Consequently, the mixture solution is derived from the top face to the bottom face of the reaction container main body 20. Here, as shown in FIG. 2, the mixed solution discharge section 27 on the bottom face side of the reaction container main body 20 is connected to an outlet port section 52 of the adapter member 50. Further, the outlet port section 52 is connected to an outlet section 62 of an adapter member 60. The mixture solution produced in the flow channel of the reaction container main body 20 is thereby discharged from a mixture solution discharge port 65 formed on the bottom face (lower face in the figure) side of the adapter member 60.

EXAMPLE 2

Figure 5:
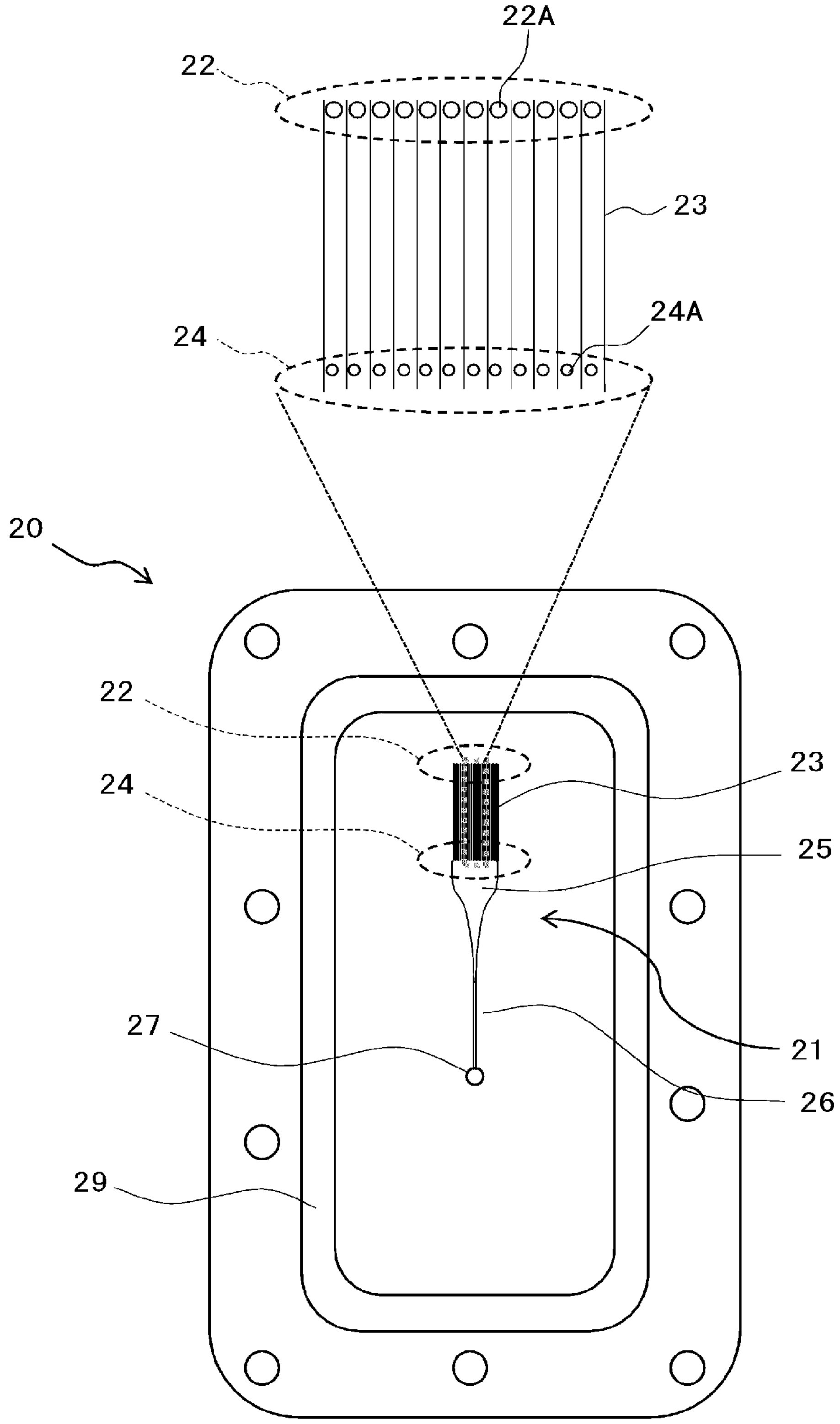
FIG. 5 is a partially enlarged view explaining a flow channel structure formed in a reaction container main body according to Example 2 of the present invention.

In the present example, a second liquid sending structure formed in a reaction container main body 20 according to Example 1 is explained. A front view of a reaction container main body 20 constituting a biomolecule radioactivity labeling reaction container 10 and a partially enlarged view of a liquid sending structure formed in the reaction container main body 20 are shown in FIG. 5.

The configuration of the reaction container main body 20 according to the present example is the same as Example 1 unless otherwise specified.

In the present example, biomolecule solution supply nozzles 22A in a biomolecule solution supply section 22 and radioactivity labeling agent solution supply nozzles 24A in a radioactivity labeling agent solution supply section 24 are formed in the same flow channels. The number of the flow channels in a biomolecule solution induction flow channel section 23 is sixty-one and a biomolecule solution 121 is supplied to a radioactivity labeling agent solidification section 25 as a laminar flow having layers about two times the layers of Example 1. As a result, interaction between the biomolecule solution 121 and a solidified radioactivity labeling agent increases and the reaction progresses rapidly.

Here, the radioactivity labeling agent solution supply nozzles 24A are formed so as to have a surface diameter not hindering the flow of the biomolecule solution 121 flowing from the upstream of the flow channels in which the nozzles are formed.

EXAMPLE 3

Figure 6A:
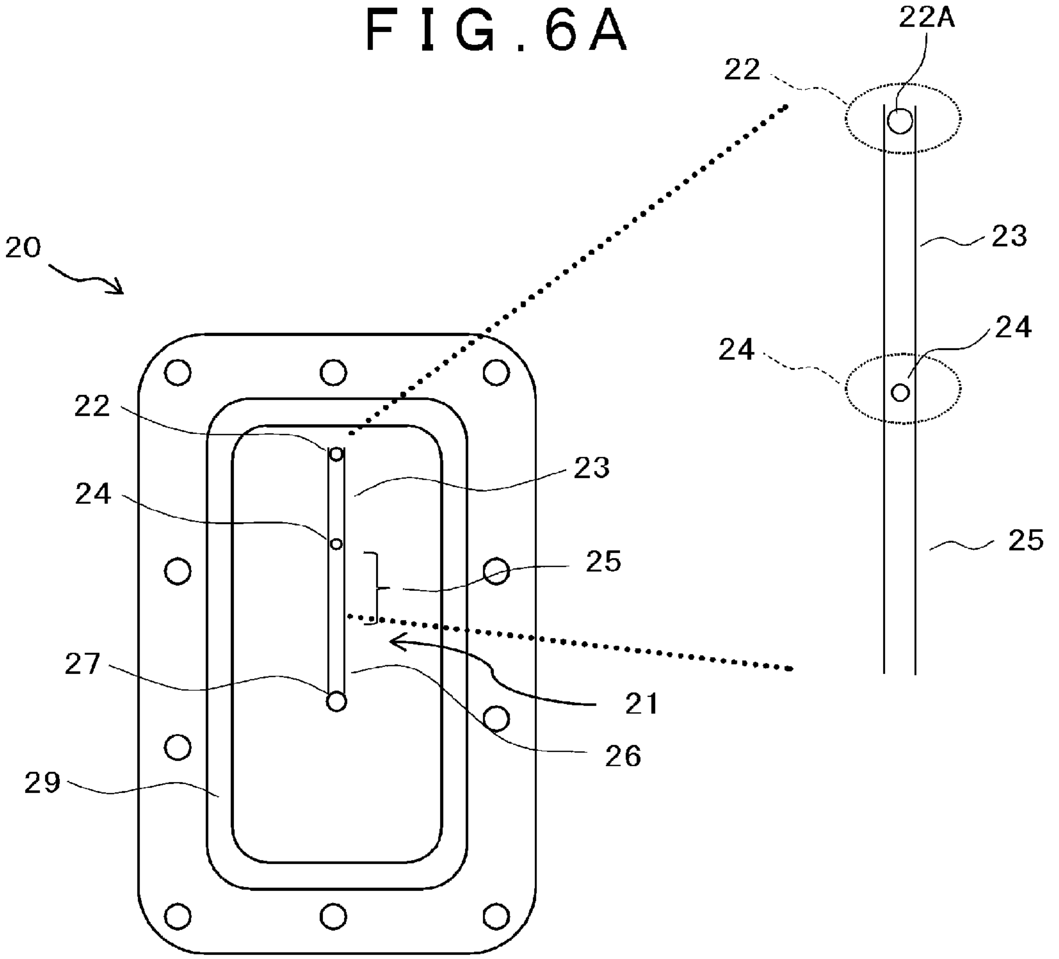
FIG. 6A includes a front view of a reaction container main body and a partially enlarged view of a flow channel explaining a flow channel structure formed in the reaction container main body according to Example 3 of the present invention.
Figure 6B:
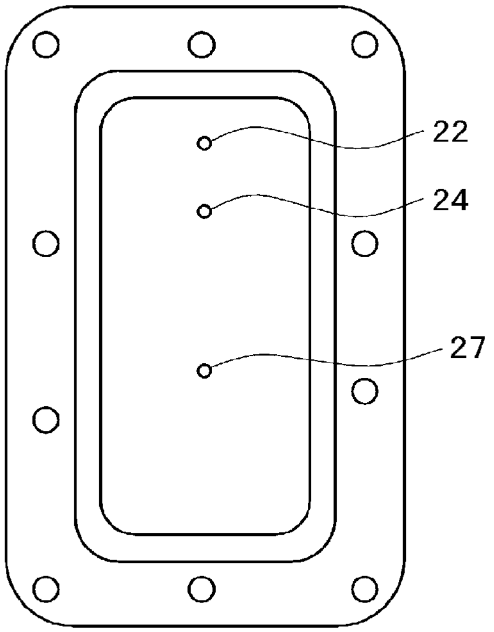
FIG. 6B is a rear view of a reaction container main body explaining a flow channel structure formed in the reaction container main body according to Example 3 of the present invention.

In the present example, a third liquid sending structure formed in a reaction container main body 20 according to Example 1 is explained. A front view and a rear view of a reaction container main body 20 constituting a biomolecule radioactivity labeling reaction container 10 and a partially enlarged view of a liquid sending structure formed in the reaction container main body 20 are shown in FIGS. 6A and 6B.

The configuration of the reaction container main body 20 according to the present example is the same as Example 1 unless otherwise specified.

A flow channel 21 in the present example has a given width, is interposed between two walls formed in parallel, and is configured as a continuous space at the intermediate section of which a radioactivity labeling agent solidification section 25 is formed. Both the ends of the flow channel include opening ends. A biomolecule solution supply section 22 to introduce a biomolecule solution 121 from the bottom face side of the reaction container main body 20 is formed at the uppermost stream section of the flow channel 21. The biomolecule solution 121 introduced from the biomolecule solution supply section 22 is induced to a mixture solution discharge section 27 located on the lower end side in the figure through the radioactivity labeling agent solidification section 25.

Here, the biomolecule solution supply section 22 includes an opening (biomolecule solution supply nozzle 22A) connecting the top face to the bottom face of the reaction container main body 20. The biomolecule solution 121 is introduced into a biomolecule solution induction flow channel section 23 through the biomolecule solution supply nozzle 22A. The opening of the biomolecule solution supply nozzle 22A on the bottom face side of the reaction container main body 20 is connected to an inlet port section 51 of an adapter member 50.

A radioactivity labeling agent solution supply section 24 is placed on the upstream side of the radioactivity labeling agent solidification section 25 and used for introducing a radioactivity labeling agent solution 122 into the radioactivity labeling agent solidification section 25. The radioactivity labeling agent solution supply section 24 includes an opening (radioactivity labeling agent solution supply nozzle 24A) connecting the top face to the bottom face of the reaction container main body 20. As shown in FIG. 6A, the radioactivity labeling agent solution supply nozzle 24A is formed so as to have a surface diameter smaller than the width of the flow channel 21 running through the biomolecule solution induction flow channel section 23, the radioactivity labeling agent solidification section 25, and a discharge side flow channel section 26. The surface diameter is decided so as not to hinder the biomolecule solution 121 introduced from the biomolecule solution induction flow channel section 23 from flowing. The radioactivity labeling agent solution 122 is introduced into the radioactivity labeling agent solidification section 25 through the radioactivity labeling agent solution supply nozzle 24A.

The radioactivity labeling agent solution supply nozzle 24A is connected to the bottom face of the reaction container main body 20 and an opening on the bottom face side is connected to the inlet port section 51 of the adapter member 50.

The radioactivity labeling agent solidification section 25 is a flow channel formed at the intermediate section of the flow channel 21. The bottom face may be formed so as to be lower than the biomolecule solution induction flow channel section 23 and the discharge side flow channel section 26. Further, although the radioactivity labeling agent solidification section 25 is formed linearly in the present example, it may also be formed into a snaky shape or a spiral shape in accordance with the capacity of the radioactivity labeling agent solution 122 introduced into the radioactivity labeling agent solidification section 25. It is thereby possible to increase the capacity of the introduced radioactivity labeling agent solution 122 reserved during the process of removing a solvent and solidifying it.

The width and the depth of the flow channel 21 formed on the top face of the reaction container main body 20 in the present example and running from the biomolecule solution induction flow channel section 23 to the radioactivity labeling agent solidification section 25, and then to the discharge side flow channel section 26 are not limited as long as they are to the extents that a radioactivity labeling agent solidified at the radioactivity labeling agent solidification section 25 does not hinder the biomolecule solution 121 from flowing. As they reduce, a surface area increases in the same capacity, interaction between the biomolecule solution 121 and the solidified radioactivity labeling agent increases, and the reaction progresses rapidly. Further, if the width and the depth of the flow channel are not larger than 1 mm, so-called microreactor effects such as the reduction of reaction time and the improvement of capability to control reaction temperature are obtained.

EXAMPLE 4

Figure 7A:
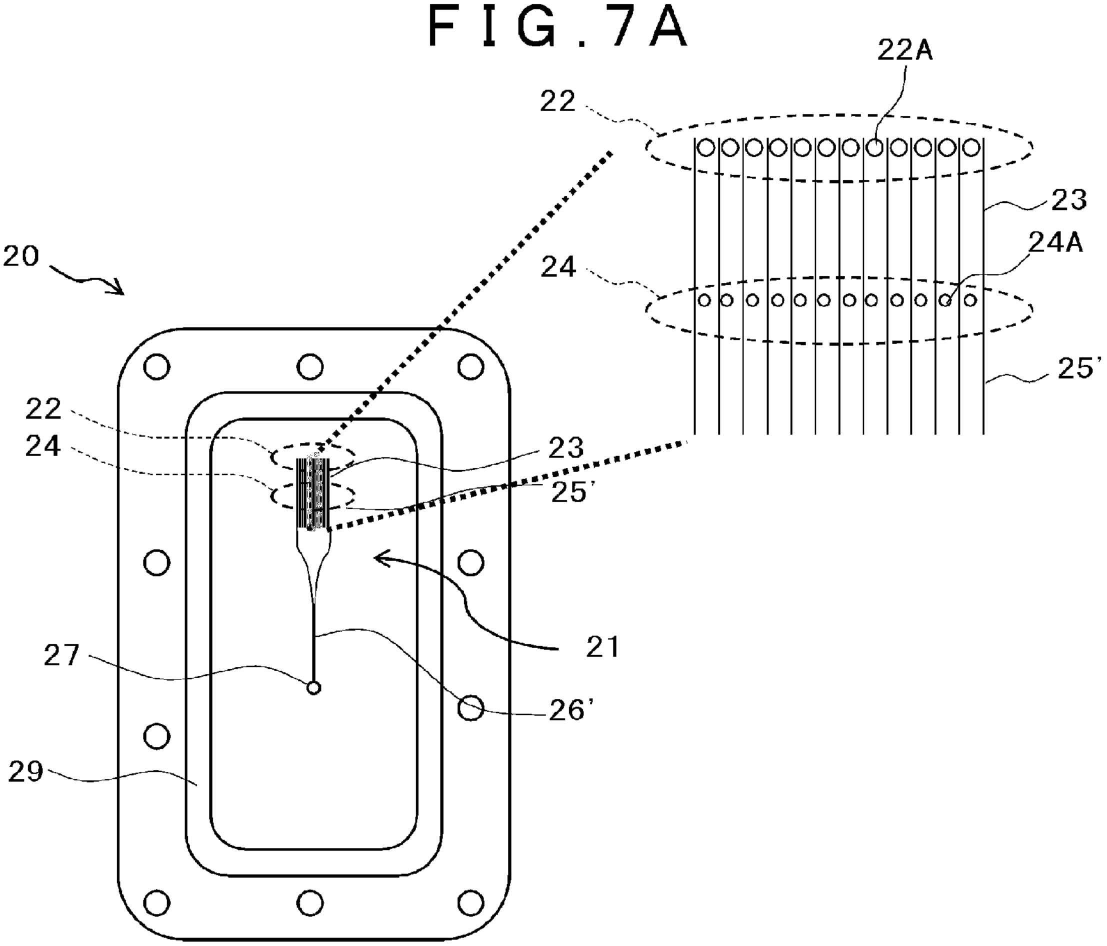
FIG. 7A includes a front view of a reaction container main body and a partially enlarged view of a flow channel explaining a flow channel structure formed in the reaction container main body according to Example 4 of the present invention.
Figure 7B:
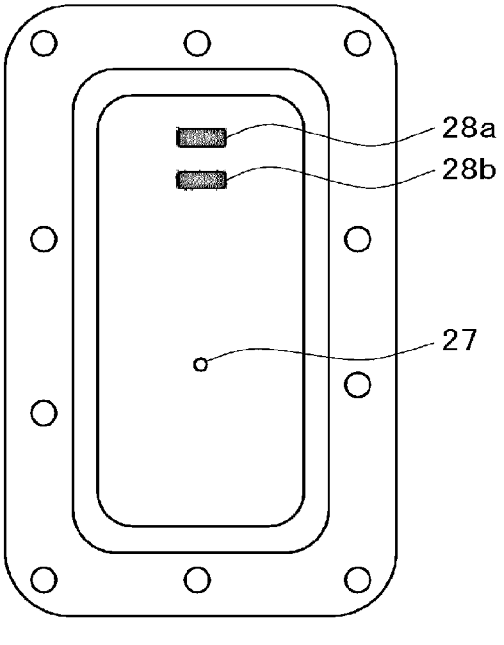
FIG. 7B is a rear view of a reaction container main body explaining a flow channel structure formed in the reaction container main body according to Example 4 of the present invention.

In the present example, a fourth liquid sending structure formed in a reaction container main body 20 according to Example 1 is explained. A front view and a rear view of a reaction container main body 20 constituting a biomolecule radioactivity labeling reaction container 10 and a partially enlarged view of a liquid sending structure formed in the reaction container main body 20 are shown in FIGS. 7A and 7B.

The configuration of the reaction container main body 20 according to the present example is the same as Example 1 unless otherwise specified.

In the present example, a radioactivity labeling agent solution supply section 24 is formed in the middle of a biomolecule solution induction flow channel section 23 in Example 2. The biomolecule solution induction flow channel section 23 below the radioactivity labeling agent solution supply section 24 is defined as a radioactivity labeling agent solidification section 25' in the present example and a funnel-shaped radioactivity labeling agent solidification section 25 and a discharge side flow channel section 26 in Example 2 are collectively defined as a discharge side flow channel section 26' in the present example.

The bottom face of the radioactivity labeling agent solidification section 25' in the present example may be formed so as to be lower than the biomolecule solution induction flow channel section 23 and the discharge side flow channel section 26'. It is thereby possible to increase the capacity of an introduced radioactivity labeling agent solution 122 reserved during the process of removing a solvent and solidifying it.

The width and the depth of a flow channel being formed on the top face of the reaction container main body 20 in the present example and running from the biomolecule solution induction flow channel section 23 to the radioactivity labeling agent solidification section 25' are not limited as long as they are to the extents that a radioactivity labeling agent solidified at the radioactivity labeling agent solidification section 25' does not hinder a biomolecule solution 121 from flowing. As they reduce, a surface area increases in the same capacity, interaction between the biomolecule solution 121 and the solidified radioactivity labeling agent increases, and the reaction progresses rapidly. Further, if the width and the depth of the flow channel are not larger than 1 mm, so-called microreactor effects such as the reduction of reaction time and the improvement of capability to control reaction temperature are obtained.

Further, in the present example, since the radioactivity labeling agent solidification section 25' where the solidified radioactivity labeling agent interacts with the biomolecule solution 121 includes a plurality of parallel flow channels, it is possible to increase a throughput in a given time while the performance in Example 3 is maintained.

EXAMPLE 5

The structure of a radiation sensor 202 formed in a biomolecule radioactivity labeling reaction container 10 in the present example is explained hereunder. The radiation sensor 202 is used for detecting radiation on a biomolecule radioactivity labeling reaction process in a biomolecule radioactivity labeling reactor 1.

Figure 8:
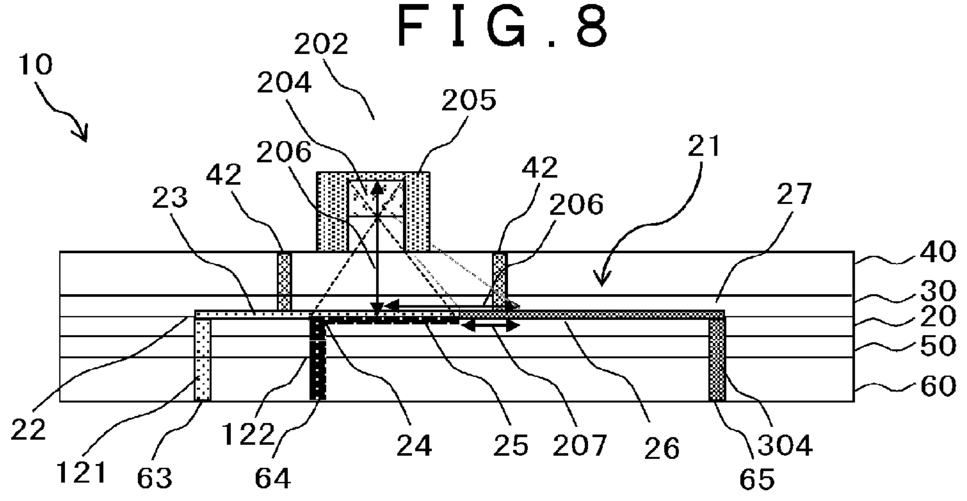
FIG. 8 is a sectional view explaining the structure of a radiation sensor formed in a biomolecule radioactivity labeling reaction container according to Example 5 of the present invention.

A sectional view of a laminated biomolecule radioactivity labeling reaction container 10 taken on a plane crossing a reaction container main body 20 shown in FIG. 2 is shown in FIG. 8.

The radiation sensor 202 in the present example includes a radiation detector 204 and a radiation shielding section 205.

The radiation sensor 202 is formed on a lid member 40 vertically above a radioactivity labeling agent solidification section 25 in a flow channel formed on the top face of the reaction container main body 20.

The sizes of the radiation detector 204 and the inlet port of the shielding section 205 on the side of the lid member 40 and the distance between the radiation detector 204 and the lid member 40 may take any values as long as the radiation of the radioactivity labeling agent solidification section 25 can be detected without being influenced by radiation emitted from a radioactive material located at sites other than the radioactivity labeling agent solidification section 25 in a biomolecule radioactivity labeling reactor 1.

Incidentally, as a distance 206 between the radiation detector 204 and the radioactivity labeling agent solidification section 25 reduces, detection sensitivity increases. Further, the radiation of a radioactive material located outside the radioactivity labeling agent solidification section 25 is detected to the extent of the distance corresponding to the distance 206 between the radiation detector 204 and the radioactivity labeling agent solidification section 25.

The shielding section 205 is formed around the outer circumference of the radiation detector 204 in order to prevent the influence of radiation emitted from a radioactive material located outside the radioactivity labeling agent solidification section 25. The material of the shielding section 205 may be any material as long as it can shield radiation emitted from a used radioactive material. As such materials, tungsten, lead, a workpiece for shielding, and others are named. Any thickness is acceptable as the thickness of a shielding material as long as it is not less than a thickness corresponding to a radiation quantity to be shielded.

In the case of the present example, the upper part of the radiation detector 204 where a radioactive material is not located is formed so as to have a thickness capable of shielding radiation emitted from the environment where the biomolecule radioactivity labeling reactor 1 is used. The right and left sides of the radiation detector 204 where a radioactive material is located are formed so as to have a thickness capable of shielding radiation emitted from a radioactive material located at a position corresponding to a length 207 obtained by subtracting a distance in the radioactivity labeling agent solidification section 25 from the distance 206 between the radiation detector 204 and the radioactivity labeling agent solidification section 25 as shown in FIG. 8.

As the width of the inlet port of the detector narrows by the shielding section 205, more radiation other than the radiation of the radioactivity labeling agent solidification section 25 is prevented from being detected. Any width is acceptable as long as the radiation of the radioactivity labeling agent solidification section 25 can be detected.

The present example makes it possible to form the radiation sensor 202 on the lid member 40 above the radioactivity labeling agent solidification section 25 in accordance with a flow channel on the reaction container main body 20 and the configuration of the biomolecule radioactivity labeling reaction container 10, and is excellent in versatility.

EXAMPLE 6

In the present example, the structure of second radiation sensors 202 formed in a biomolecule radioactivity labeling reaction container 10 as a modification of Example 5 is explained.

Figure 9:
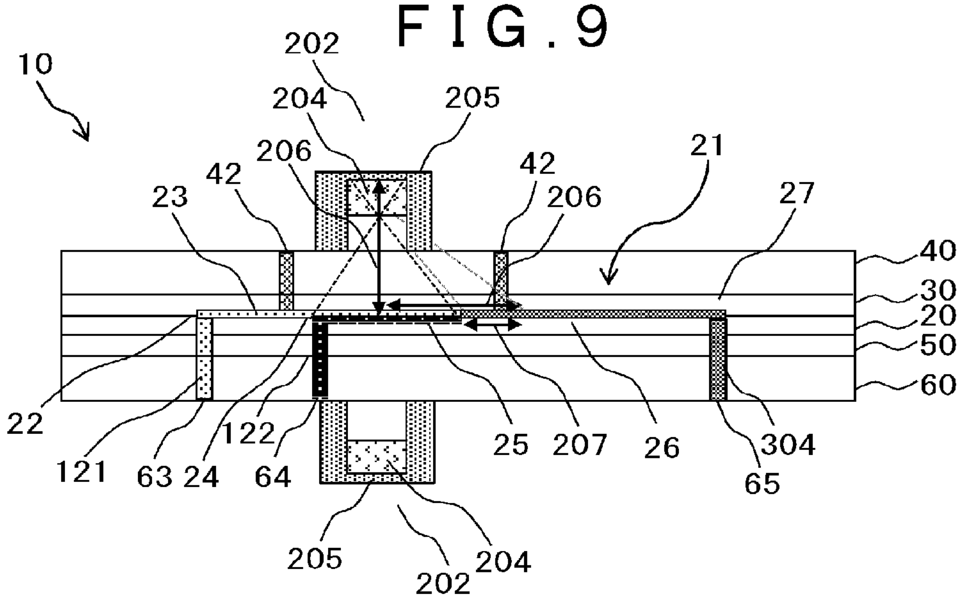
FIG. 9 is a sectional view explaining the structure of radiation sensors formed in a biomolecule radioactivity labeling reaction container according to Example 6 of the present invention.

A sectional view of a laminated biomolecule radioactivity labeling reaction container 10 taken on a plane crossing a reaction container main body 20 shown in FIG. 2 is shown in FIG. 9. Points not specified are the same as those in Example 5.

In the present example, another radiation sensor 202 that is the same as a radiation sensor 202 formed on a lid member 40 in Example 5 is formed on an adapter member 60 in the manner of facing each other.

In the present example, high detection sensitivity is obtained by using the two radiation detectors 204 in the manner of facing each other.

When a radioactivity labeling agent is a positron nuclide, a shielding section 205 becomes unnecessary by applying coincidence counting.

EXAMPLE 7

In the present example, the structure of third radiation sensors 202 formed in a biomolecule radioactivity labeling reaction container 10 as a modification of Example 5 is explained.

Figure 10:
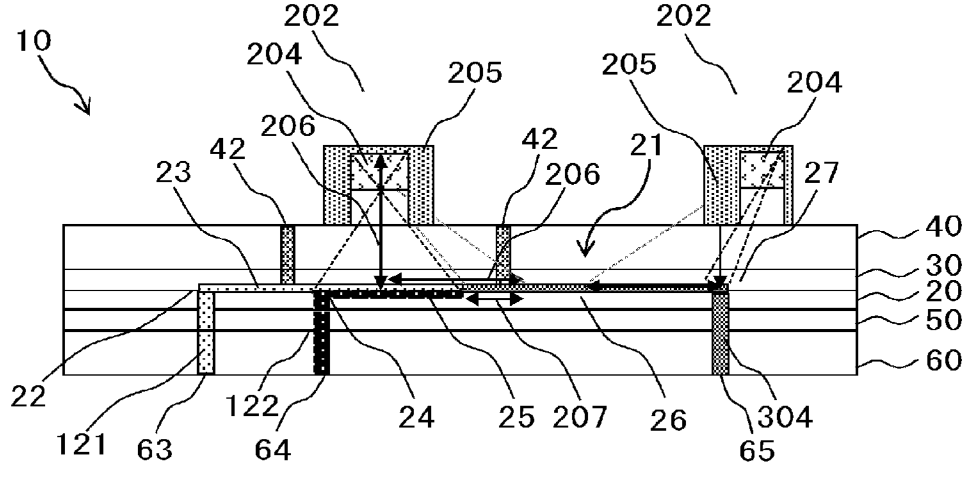
FIG. 10 is a sectional view explaining the structure of radiation sensors formed in a biomolecule radioactivity labeling reaction container according to Example 7 of the present invention.

A sectional view of a laminated biomolecule radioactivity labeling reaction container 10 taken on a plane crossing a reaction container main body 20 shown in FIG. 2 is shown in FIG. 10. Points not specified are the same as those in Example 5.

In the present example, another radiation sensor 202 that is the same as a radiation sensor 202 formed on a lid member 40 above a radioactivity labeling agent solidification section 25 in Example 6 is formed on a lid member 40 above a mixture solution discharge section 27.

In the present example, it is possible to monitor the progress of reaction by two means by using the two radiation detectors 204 located at different positions. That is, it is possible to monitor the quantity of a radioactivity labeling agent dissolving in a biomolecule solution 121 and decaying by using the radiation sensor 202 formed above the radioactivity labeling agent solidification section 25 and to monitor the quantity of a radioactive material increasing in a mixture solution 304 by using the radiation sensor 202 formed above the mixture solution discharge section 27.

EXAMPLE 8

In the present example, the structure of a fourth radiation sensor 202 formed in a biomolecule radioactivity labeling reaction container 10 as a modification of Example 5 is explained.

Figure 11:
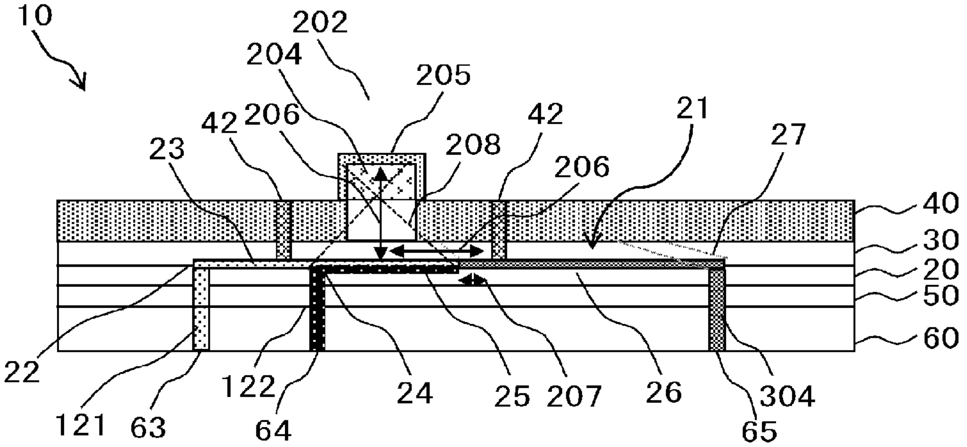
FIG. 11 is a sectional view explaining the structure of a radiation sensor formed in a biomolecule radioactivity labeling reaction container according to Example 8 of the present invention.

A sectional view of a laminated biomolecule radioactivity labeling reaction container 10 taken on a plane crossing a reaction container main body 20 shown in FIG. 2 is shown in FIG. 11. Points not specified are the same as those in Example 5.

In the present example, a lid member 40 includes shielding tungsten. As such a material, any material may be used as long as it can shield radiation emitted from a used radioactive material. Lead, concrete, a workpiece for shielding, and others are named in addition to tungsten. As the thickness of the lid member 40, any thickness is acceptable as long as it is not less than a thickness: corresponding to a radiation quantity to be shielded; and being capable of keeping a flow channel formed on the reaction container main body 20 in the laminated layer of the radioactivity labeling reaction container 10.

In the present example, a space section 208 to detect radiation emitted from a radioactivity labeling agent solidification section 25 is formed in the lid member 40. The space section 208 pierces through the lid member 40 and is formed so as to have a width capable of detecting radiation of the radioactivity labeling agent solidification section 25 and capable of shielding radiation of a radioactive material corresponding to a length 207 obtained by subtracting the distance of the radioactivity labeling agent solidification section 25 from a distance 206 between 204 and the radioactivity labeling agent solidification section 25 shown in FIG. 11.

A shielding section 205 formed on the upper part and both the sides of the radiation detector 204 is formed so as to have a thickness capable of shielding radiation emitted from the environment where a biomolecule radioactivity labeling reactor 1 is used.

The present example can be applicable also to a reaction container main body 20 of a different flow channel type as long as the position of a radioactivity labeling agent solidification section 25 is not changed in the flow channel on the reaction container main body 20, and can simplify the structure of a shielding section 205.

EXAMPLE 9

In the present example, the structure of fifth radiation sensors 202 formed in a biomolecule radioactivity labeling reaction container 10 as a modification of Example 8 is explained.

Figure 12:
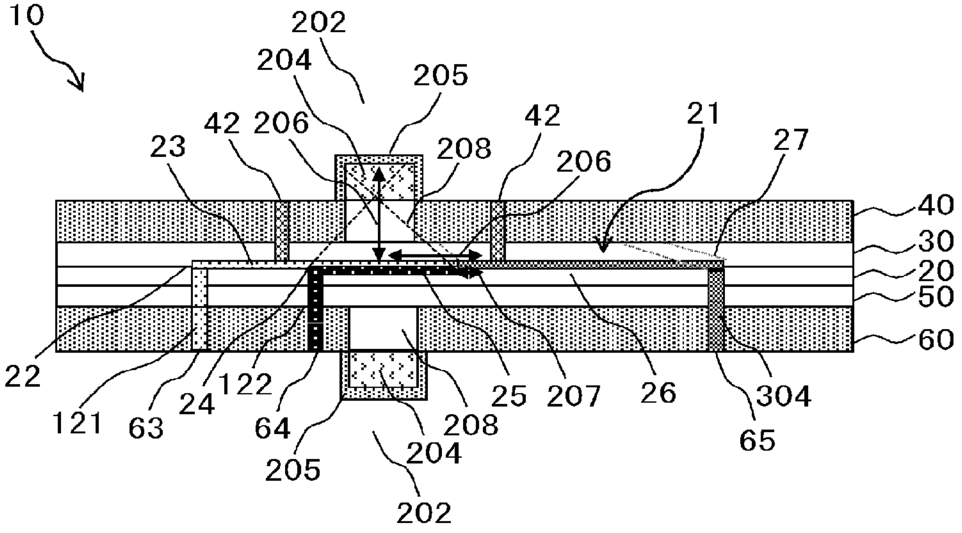
FIG. 12 is a sectional view explaining the structure of radiation sensors formed in a biomolecule radioactivity labeling reaction container according to Example 9 of the present invention.

A sectional view of a laminated biomolecule radioactivity labeling reaction container 10 taken on a plane crossing a reaction container main body 20 shown in FIG. 2 is shown in FIG. 12. Points not specified are the same as those in Example 8.

In the present example, another radiation sensor 202 that is the same as a radiation sensor 202 formed in a lid member 40 in Example 8 is formed in an adapter member 60 in the manner of facing each other.

In response to that, in the present example, the adapter member 60 includes tungsten. Further, another space section 208 to detect radiation emitted from a radioactivity labeling agent solidification section 25 is formed in the adapter member 60.

In the present example, high detection sensitivity is obtained by using the two radiation detectors 204 in the manner of facing each other.

EXAMPLE 10

In the present example, the structure of sixth radiation sensors 202 formed in a biomolecule radioactivity labeling reaction container 10 as a modification of Example 8 is explained.

Figure 13:
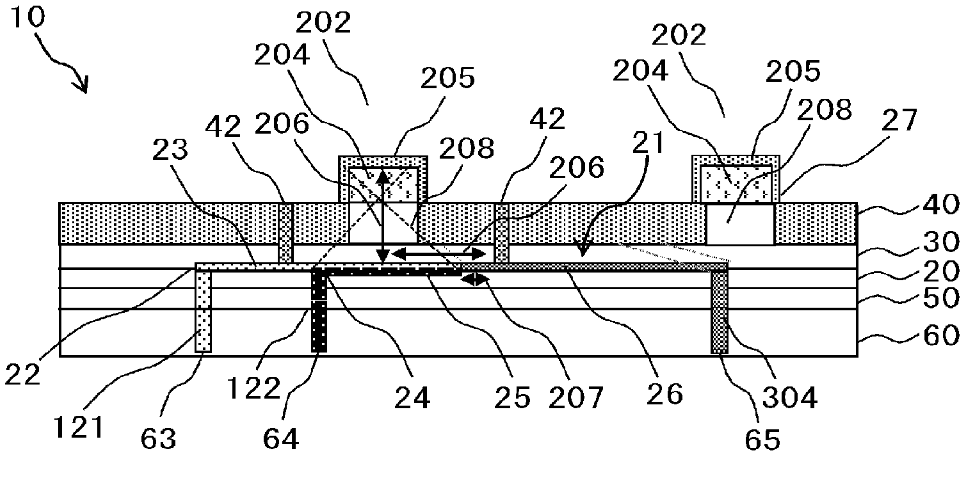
FIG. 13 is a sectional view explaining the structure of radiation sensors formed in a biomolecule radioactivity labeling reaction container according to Example 10 of the present invention.

A sectional view of a laminated biomolecule radioactivity labeling reaction container 10 taken on a plane crossing a reaction container main body 20 shown in FIG. 2 is shown in FIG. 13. Points not specified are the same as those in Example 8.

In the present example, another radiation sensor 202 that is the same as a radiation sensor 202 formed in a lid member 40 above a radioactivity labeling agent solidification section 25 in Example 8 is formed in a lid member 40 above a mixture solution discharge section 27. In response to that, another space section 208 to detect radiation of the mixture solution discharge section 27 is formed in the lid member 40 above the mixture solution discharge section 27.

In the present example, it is possible to monitor the progress of reaction by two means by using the two radiation detectors 204 located at different positions. That is, it is possible to monitor the quantity of a radioactivity labeling agent dissolving in a biomolecule solution 121 and decaying by using the radiation sensor 202 formed above the radioactivity labeling agent solidification section 25 and to monitor the quantity of a radioactive material increasing in a mixture solution 304 by using the radiation sensor 202 formed above the mixture solution discharge section 27.

EXAMPLE 11

In the present example, the structure of a seventh radiation sensor 202 formed in a biomolecule radioactivity labeling reaction container 10 as a modification of Example 5 is explained.

Figure 14:
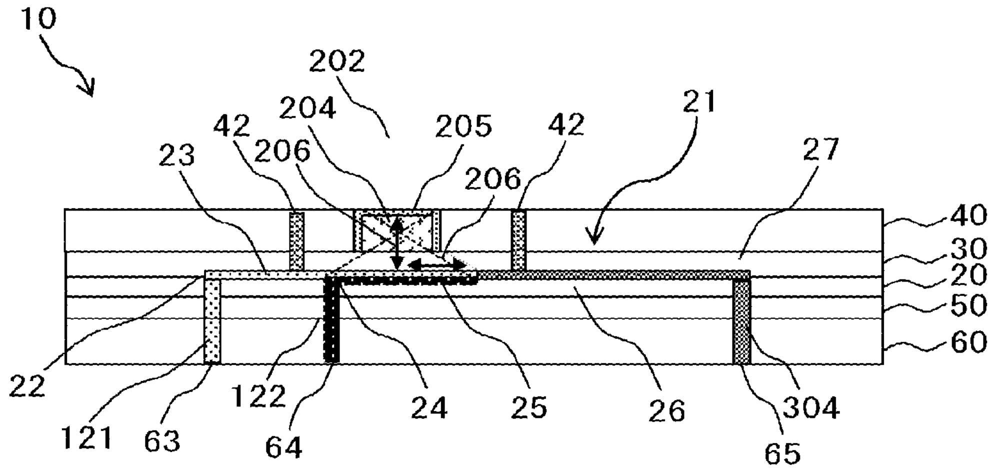
FIG. 14 is a sectional view explaining the structure of a radiation sensor formed in a biomolecule radioactivity labeling reaction container according to Example 11 of the present invention.

A sectional view of a laminated biomolecule radioactivity labeling reaction container 10 taken on a plane crossing a reaction container main body 20 shown in FIG. 2 is shown in FIG. 14. Points not specified are the same as those in Example 5.

In the present example, a radiation sensor 202 is formed in a lid member 40. In the present example, by appropriately setting the opening width of a shielding section 205 on the side of a radioactivity labeling agent solidification section 25, it is possible to form the shielding section 205 so as to have a thickness capable of shielding radiation emitted from the environment where a biomolecule radioactivity labeling reactor 1 is used.

Further, since a distance 206 between a radiation detector 204 and the radioactivity labeling agent solidification section 25 is small, high detection sensitivity is obtained.

EXAMPLE 12

In the present example, the structure of eighth radiation sensors 202 formed in a biomolecule radioactivity labeling reaction container 10 as a modification of Example 11 is explained.

Figure 15:
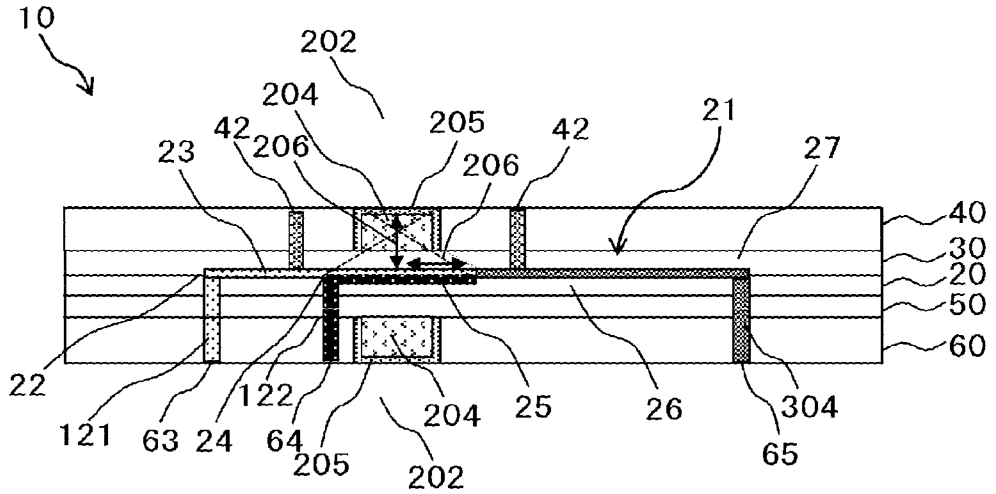
FIG. 15 is a sectional view explaining the structure of radiation sensors formed in a biomolecule radioactivity labeling reaction container according to Example 12 of the present invention.

A sectional view of a laminated biomolecule radioactivity labeling reaction container 10 taken on a plane crossing a reaction container main body 20 shown in FIG. 2 is shown in FIG. 15. Points not specified are the same as those in Example 11.

In the present example, another radiation sensor 202 that is the same as a radiation sensor 202 formed in a lid member 40 in Example 11 is formed in an adapter member 60 in the manner of facing each other.

In the present example, higher detection sensitivity is obtained by using the two radiation detectors 204 in the manner of facing each other.

When a radioactivity labeling agent is a positron nuclide, a shielding section 205 becomes unnecessary by applying coincidence counting.

EXAMPLE 13

In the present example, the structure of ninth radiation sensors 202 formed in a biomolecule radioactivity labeling reaction container 10 as a modification of Example 11 is explained.

Figure 16:
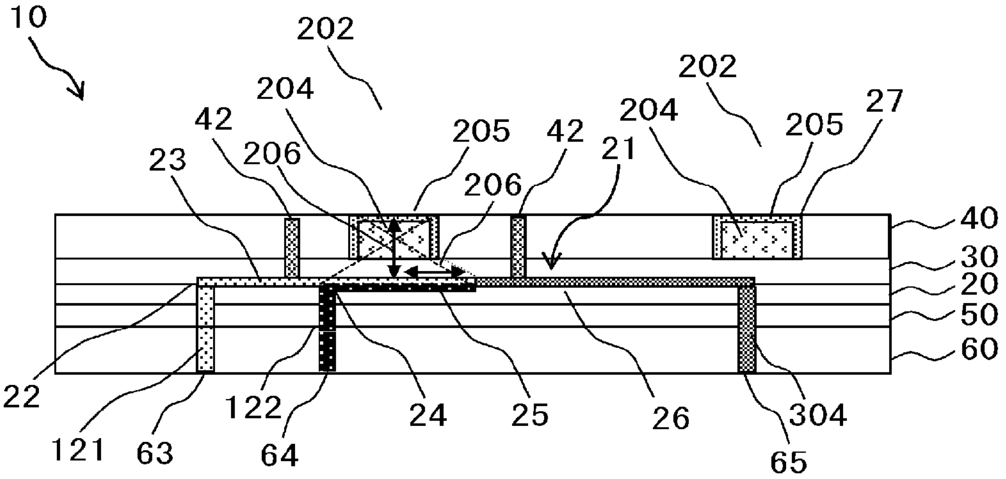
FIG. 16 is a sectional view explaining the structure of radiation sensors formed in a biomolecule radioactivity labeling reaction container according to Example 13 of the present invention.

A sectional view of a laminated biomolecule radioactivity labeling reaction container 10 taken on a plane crossing a reaction container main body 20 shown in FIG. 2 is shown in FIG. 16. Points not specified are the same as those in Example 11.

In the present example, another radiation sensor 202 that is the same as a radiation sensor 202 formed in a lid member 40 above a radioactivity labeling agent solidification section 25 in Example 11 is formed in a lid member 40 above a mixture solution discharge section 27.

In the present example, it is possible to monitor the progress of reaction by two means by using the two radiation detectors 204 located at different positions. That is, it is possible to monitor the quantity of a radioactivity labeling agent dissolving in a biomolecule solution 121 and decaying by using the radiation sensor 202 formed above the radioactivity labeling agent solidification section 25 and to monitor the quantity of a radioactive material increasing in a mixture solution 304 by using the radiation sensor 202 formed above the mixture solution discharge section 27.

EXAMPLE 14

Figure 17:
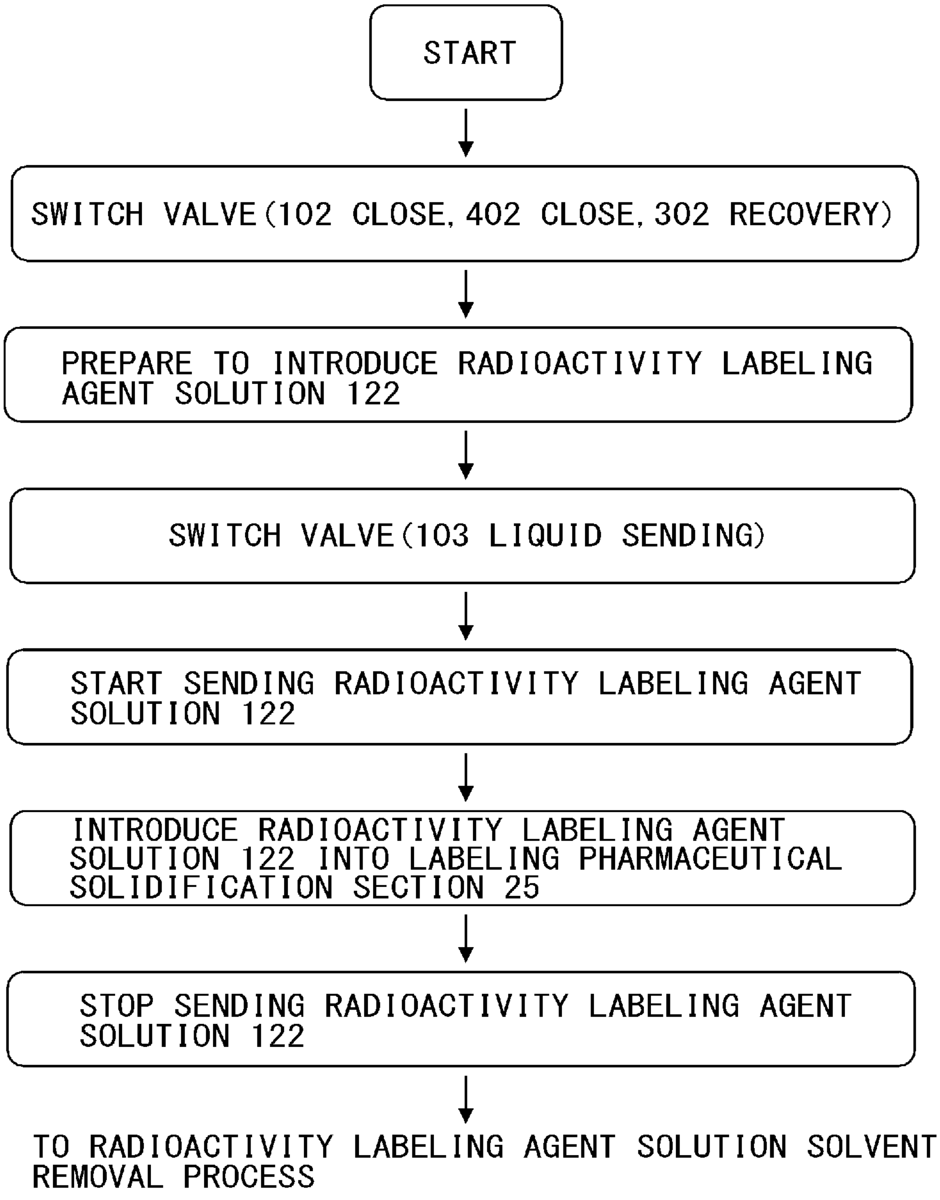
FIG. 17 is a flowchart explaining the processes of introducing a radioactivity labeling agent solution into a biomolecule radioactivity labeling reactor according to Example 14 of the present invention.
Figure 18:
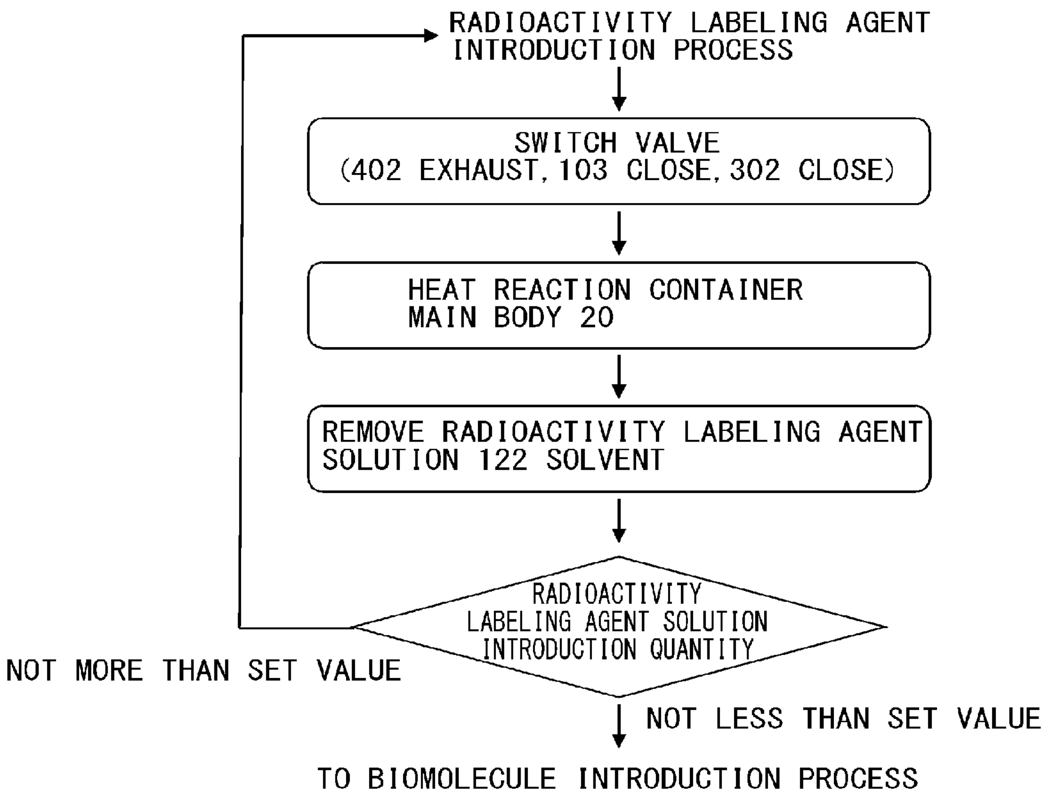
FIG. 18 is a flowchart explaining the processes of removing a solvent in a radioactivity labeling agent solution with a biomolecule radioactivity labeling reactor according to Example 14 of the present invention.
Figure 19:
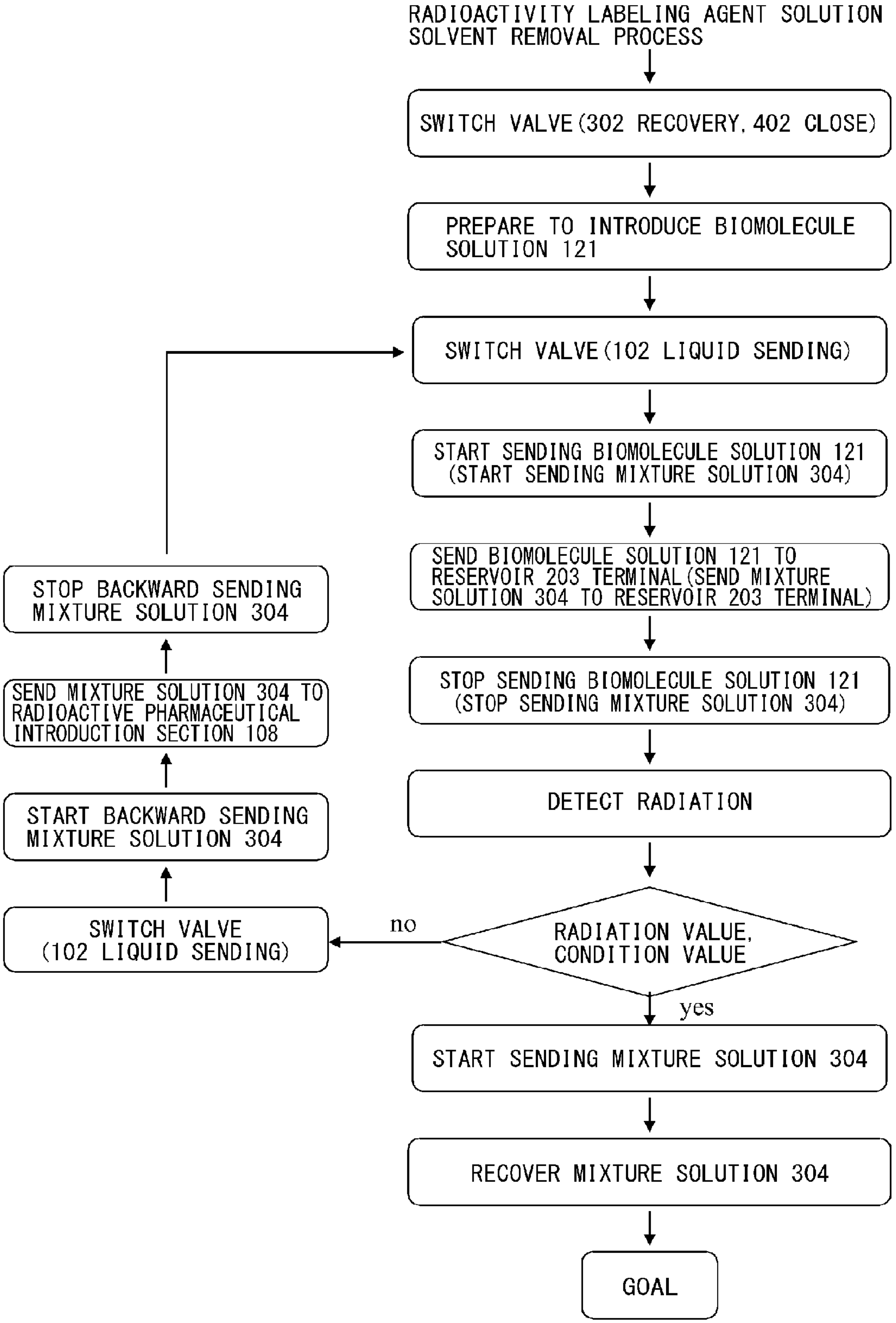
FIG. 19 is a flowchart explaining the processes of introducing a biomolecule solution into a biomolecule radioactivity labeling reactor according to Example 14 of the present invention and then performing a biomolecule radioactivity labeling reaction.

The processes of radioactivity labeling reaction of a biomolecule processed in a reaction container main body 20 are explained hereunder in reference to FIGS. 1 to 4 and 17 to 19. The processes of introducing a radioactivity labeling agent solution are shown in FIG. 17, the processes of removing a solvent of the radioactivity labeling agent solution are shown in FIG. 18, and the processes of introducing a biomolecule solution to the processes of applying biomolecule radioactivity labeling reaction are shown in FIG. 19.

[Processes of Introducing Radioactivity Labeling Agent Solution and Removing Solvent]

Firstly, the processes of introducing a radioactivity labeling agent solution 122 into a biomolecule radioactivity labeling reaction container 10 and the processes of removing a solvent of the radioactivity labeling agent solution 122 are explained in reference to FIGS. 1 to 4, 17, and 18.

Firstly, a liquid sending switch valve 102 and exhausting switch valves 402 are closed and a recovery switch valve 302 is switched to recovery.

Successively, the setting of a liquid sending switch valve 103 is switched so as to send a radioactivity labeling agent solution 122 sucked from a solution sucking line 104 to a syringe 106. Successively, a syringe pump 107 is drawn downward in the figure and the radioactivity labeling agent solution 122 is introduced into the syringe 106 through the solution sucking line 104 and the liquid sending switch valve 103.

After the radioactivity labeling agent solution 122 is introduced into the syringe 106, the liquid sending switch valve 103 is switched so as to send the radioactivity labeling agent solution 122 from the syringe 106 toward a radioactivity labeling agent solution introduction section 109.

After the switching, the syringe pump 107 on the side of the radioactivity labeling agent solution is pushed upward in the figure and the radioactivity labeling agent solution 122 in the syringe 106 is sent to a biomolecule radioactivity labeling reaction container 10 through the liquid sending switch valve 103 and the radioactivity labeling agent solution introduction section 109.

The radioactivity labeling agent solution 122 sent from the radioactivity labeling agent solution introduction section 109 is introduced into the biomolecule radioactivity labeling reaction container 10 from a radioactivity labeling agent solution introduction port 64 formed on the bottom side face of an adapter member 60. The radioactivity labeling agent solution introduction port 64 is formed so as to have a large diameter in order to attach a socket not shown in the figures and induces the radioactivity labeling agent solution 122 to a radioactivity labeling agent solution accumulation section **28*b* through the adapter member 60, a small hole of an adapter member 50, and an inlet port section 51 formed on the top side face of the adapter member 50**.

The radioactivity labeling agent solution accumulation section **28*b* has a minimum capacity allowing the radioactivity labeling agent solution 122 to be supplied to all radioactivity labeling agent solution supply nozzles 24**A at an equal pressure.

The radioactivity labeling agent solution 122 with which the radioactivity labeling agent solution accumulation section **28*b* is filled is supplied to the radioactivity labeling agent solution supply nozzles 24A at an equal pressure. As a result, the radioactivity labeling agent solution 122 is ejected from all the radioactivity labeling agent solution supply nozzles 24A nearly equally and induced from the radioactivity labeling agent solution supply nozzles 24A to a radioactivity labeling agent solidification section 25**.

The radioactivity labeling agent solution supply nozzles 24A are formed at a radioactivity labeling agent solution supply section 24 located at the end section (the lowest section) of a biomolecule solution induction flow channel section 23 as shown in FIG. 4. The radioactivity labeling agent solution supply nozzles 24A deviate from biomolecule solution supply nozzles 22A at a distance corresponding to the size of one nozzle in the width direction of a reaction container main body 20. The surface diameter of the radioactivity labeling agent solution supply nozzles 24A is nearly the same as the width and the depth of each of the flow channels of the biomolecule solution induction flow channel section 23.

After the introduction of the radioactivity labeling agent solution 122 into the radioactivity labeling agent solidification section 25 is confirmed by the increase of a radiation quantity with a radiation sensor 202, the exhausting switch valve 402 is switched to the exhausting direction and the liquid sending switch valve 103 and the recovery switch valve 302 are switched to close.

The biomolecule radioactivity labeling reaction container 10 is heated with a temperature regulating unit 501 and a solvent of the radioactivity labeling agent solution 122 is removed.

The quantity of the radioactivity labeling agent solution 122 introduced into the biomolecule radioactivity labeling reaction container 10 is set at a capacity of filling the radioactivity labeling agent solidification section 25. When a necessary quantity of the radioactivity labeling agent solution 122 is not less than the capacity, the processes of introducing the radioactivity labeling agent solution 122 into the radioactivity labeling agent solidification section 25 and removing the solvent of the radioactivity labeling agent solution 122 are repeated until the quantity of the radioactivity labeling agent solution 122 introduced into the radioactivity labeling agent solidification section 25 reaches a necessary quantity.

After the quantity of the radioactivity labeling agent solution 122 introduced into the radioactivity labeling agent solidification section 25 reaches a necessary quantity, the radioactivity labeling agent solution 122 remaining in the radioactivity labeling agent solution introduction section 109 and the syringe 106 before the biomolecule radioactivity labeling reaction container 10 may be discharged and they may be filled with a solvent or air. By applying this process, it is possible to prevent the influence of the radioactivity labeling agent solution 122 remaining in the radioactivity labeling agent solution introduction section 109 and the syringe 106 when radiation during reaction is monitored. Further, by filling them with a solvent, a reverse flow to the radioactivity labeling agent solution introduction section 109 can be prevented when a biomolecule solution 121 is reciprocally sent.

The processes are more secured by confirming the existence of outflow of the radioactivity labeling agent solution 122 to other than the radioactivity labeling agent solidification section 25 with a radiation sensor 202 (Examples 7, 10, and 13 for example) separately formed and not shown in the figures in the process of introducing the radioactivity labeling agent solution 122 into the biomolecule radioactivity labeling reaction container 10.

When the outflow of the radioactivity labeling agent solution 122 to other than the radioactivity labeling agent solidification section 25 is confirmed, the liquid sending switch valve 103 is switched so as to send the radioactivity labeling agent solution 122 from the biomolecule radioactivity labeling reaction container 10 toward the syringe 106. After the switching, the syringe pump 107 on the side of the radioactivity labeling agent solution is pushed downward in the figure and the radioactivity labeling agent solution 122 in the biomolecule radioactivity labeling reaction container 10 is recovered in the syringe 106 through the radioactivity labeling agent solution introduction section 109 and the liquid sending switch valve 103. When there is the possibility that the radioactivity labeling agent solution 122 is contaminated by impurities in the biomolecule radioactivity labeling reaction container 10, the liquid sending switch valve 103 is kept in the liquid sending state and the recovery switch valve 302 is kept in the recovery state, the syringe pump 107 on the side of the radioactivity labeling agent solution is pushed upward in the figure, and the radioactivity labeling agent solution 122 in the biomolecule radioactivity labeling reaction container 10 is recovered through a reservoir section 203 and a mixture solution recovery line 303.

At the process of removing a solvent of the radioactivity labeling agent solution 122, the heating temperature is set at around the boiling point of the solvent of the radioactivity labeling agent solution 122. Further, the heating time is set at a time enough to remove the solvent. By confirming the time necessary for removing the solvent at a preliminary test, it is possible to set a minimum necessary time at the actual process. Further, by introducing a gas from a biomolecule solution introduction section 108 and confirming that the detected radiation quantity of the radioactivity labeling agent solidification section 25 does not vary with a radiation sensor 202, it is possible to confirm that the solvent removal of the radioactivity labeling agent solution 122 is finished.

At the process of removing the solvent of the radioactivity labeling agent solution 122, a method of introducing a gas or reducing pressure may also be used in place of the method of heating the biomolecule radioactivity labeling reaction container 10.

When a method of introducing a gas is used at the process of removing the solvent of the radioactivity labeling agent solution 122, one of exhausting lines 403 is used as a gas sending line and connected to a gas supply source. As such supply sources, a gas line, a gas cylinder, a balloon storing a gas, and others are named. As a gas, any gas can be used as long as the gas does not affect the reaction occurring in the biomolecule radioactivity labeling reaction container 10. As such gasses, atmospheric air, nitrogen, argon, and others are named. The exhausting switch valve 402 on the side connected to the gas sending line is switched to the direction of sending a gas to the biomolecule radioactivity labeling reaction container 10 through the exhausting lines 403 and the gas is introduced into the biomolecule radioactivity labeling reaction container 10 from the gas supply source through the exhausting line 403 and the exhausting switch valve 402. The introduced quantity is set at a quantity of the extent of not allowing the solvent of the radioactivity labeling agent solution 122 to be discharged from a discharge outlet port section 31.

When a method of reducing pressure is used at the process of removing the solvent of the radioactivity labeling agent solution 122, the exhausting line 403 is connected to a vacuum unit. As such vacuum units, a vacuum pump, an aspirator, and others are named. The degree of pressure reduction is set at an extent of not allowing the solvent of the radioactivity labeling agent solution 122 to be discharged from the discharge outlet port section 31.

Through the above processes, the radioactivity labeling agent solution 122 is introduced into the biomolecule radioactivity labeling reaction container 10 and the solvent of the radioactivity labeling agent solution 122 is removed.

[Processes of Introducing Biomolecule Solution and Reaction]

The processes of introducing the biomolecule solution 121 into the biomolecule radioactivity labeling reaction container 10 and reacting a biomolecule with a radioactivity labeling agent are explained hereunder in reference to FIGS. 1 to 4 and 19.

Firstly, the recovery switch valve 302 is switched to recovery and the exhausting switch valves 402 are switched to close.

Successively, the setting of the liquid sending switch valve 102 is switched so as to send the biomolecule solution 121 sucked from a solution sucking line 104 to a syringe 106. Successively, a syringe pump 107 is drawn downward in the figure and the biomolecule solution 121 is introduced into the syringe 106 through the solution sucking line 104 and the liquid sending switch valve 102.

After the biomolecule solution 121 is introduced into the syringe 106, the liquid sending switch valve 102 is switched so as to send the biomolecule solution 121 from the syringe 106 toward the biomolecule solution introduction section 108.

After the switching, the syringe pump 107 on the side of the biomolecule solution is pushed upward in the figure and the biomolecule solution 121 in the syringe 106 is introduced into the biomolecule radioactivity labeling reaction container 10 through the liquid sending switch valve 102 and the biomolecule solution introduction section 108.

The biomolecule solution 121 sent from the biomolecule solution introduction section 108 is introduced into the biomolecule radioactivity labeling reaction container 10 from a biomolecule solution introduction port 63 formed on the bottom side face of the adapter member 60. The biomolecule solution introduction port 63 is formed so as to have a large diameter in order to attach a socket not shown in the figure and the biomolecule solution 121 is introduced into a biomolecule solution accumulation section **28*a* through the adapter member 60, a small hole of the adapter member 50, and the inlet port section 51 formed on the top side face of the adapter member 50**.

The biomolecule solution accumulation section **28*a* has a minimum capacity allowing the biomolecule solution 121 to be supplied to all the biomolecule solution supply nozzles 22**A at an equal pressure.

The biomolecule solution 121 with which the biomolecule solution accumulation section **28*a* is filled is supplied to all the biomolecule solution supply nozzles 22A at an equal pressure. As a result, the biomolecule solution 121 is ejected from all the biomolecule solution supply nozzles 22A nearly equally and induced from the biomolecule solution supply nozzles 22A to the biomolecule solution induction flow channel section 23**.

The flow channel width of the biomolecule solution induction flow channel section 23 is nearly the same as the surface diameter of the biomolecule solution supply nozzles 22A and the flow channel depth is also nearly the same. After the biomolecule solution 121 flows in the flow channel of a length ten and several times the flow channel width, the biomolecule solution 121 outflows to the radioactivity labeling agent solidification section 25 having a funnel-shaped flow channel width.

At the biomolecule solution induction flow channel section 23 to which the biomolecule solution 121 introduced from a biomolecule solution supply section 22 is induced, a space of a width identical to the width of each flow channel is formed between two first flow channels constituting the biomolecule solution induction flow channel section 23 in the longitudinal direction (direction of the flow of the solution) of the reaction container main body 20 from the positions of the biomolecule solution supply nozzles 22A in the manner of flowing individually as many strip-shaped flows of the biomolecule solution 121. The spaces are called second flow channels in the present example. In this way, since the biomolecule solution supply nozzles 22A and the radioactivity labeling agent solution supply nozzles 24A are placed in the manner of alternately deviating from each other in the width direction, the biomolecule solution 121 ejected from many biomolecule solution supply nozzles 22A forms a multi-layer flow flowing in a strip shape at the radioactivity labeling agent solidification section 25.

The biomolecule solution 121 passes through a radioactivity labeling agent solidified in the radioactivity labeling agent solidification section 25 and flows into a discharge side flow channel section 26 as a multi-layer flow.

As the multi-layer flow formed in the radioactivity labeling agent solidification section 25 flows in the longitudinal direction (direction of the flow of the solution) of the reaction container main body 20, the cross-sectional area in the width direction of each of the fragmented flows reduces and the multi-layer flow comes to be an accelerated flow and flows into the discharge side flow channel section 26. That is, while the multi-layer flow shifts from the radioactivity labeling agent solidification section 25 toward the discharge side flow channel section 26, the width of the flow of the solution gradually reduces in the direction vertical to the contact interfaces of the multi-layer flow and the length in the width direction of each of the solution layers constituting the multi-layer flow reduces.

The discharge side flow channel section 26 is a flow channel extending in the longitudinal direction of the reaction container main body 20 and the end thereof reaches a mixture solution discharge section 27. With regard to the length of the discharge side flow channel section 26, any length is acceptable as long as it is a length that can secure time necessary for mixing the biomolecule solution 121 with the radioactivity labeling agent. Consequently, the flow channel width and length of the discharge side flow channel section 26 may be decided in accordance with the diffusion time of the biomolecule solution 121 and the radioactivity labeling agent and the shape is not necessarily linear as shown in FIG. 3A. For example, it may also be formed into a snaky shape or a spiral shape. A plurality of holes are formed at an outlet port section 52 of the adapter member 50 and an outlet section 62 of the adapter member 60 so that the flow channel length is changeable in accordance with the intended use.

When the mixture of the biomolecule solution 121 and the radioactivity labeling agent solution 122 is sent from the discharge side flow channel section 26 formed in the center at the lower section of the reaction container main body 20 to the entry of the recovery switch valve 302 at the end of the reservoir section 203 through the outlet port section 52 of the adapter member 50, the outlet section 62 of the adapter member 60, and a mixture solution discharge port 65, the syringe pump 107 stops and the liquid sending stops.

The radiation remaining in the radioactivity labeling agent solidification section 25 is detected with a radiation sensor 202.

Successively, the setting of the liquid sending switch valve 102 is switched so as to reversely send the biomolecule solution 121 from the reservoir section 203 toward the flow channel 21. Successively, when the syringe pump 107 is drawn downward in the figure and the biomolecule solution 121 having reached the end of the reservoir section 203 is sent to the biomolecule solution introduction section 108 through the discharge side flow channel section 26, the radioactivity labeling agent solidification section 25, and the biomolecule solution induction flow channel section 23, the syringe pump 107 stops and the liquid sending stops.

The above operations are repeated until the quantity of the radiation emitted from the radioactivity labeling agent solidification section 25 reaches a value not more than a preset value. When the quantity of the radiation remaining in the radioactivity labeling agent solidification section 25 reaches the preset value, the mixed solution which is reciprocally sent between the radioactivity labeling agent solidification section 25 and the reservoir section 203 is recovered from the mixture solution recovery line through the recovery switch valve 302, the syringe pump 107 stops, and the liquid sending stops.

In the reciprocal liquid sending process, radiation is detected every time when the liquid is sent reciprocally and it is also possible to compute the frequency of reciprocal liquid sending until the preset radiation quantity is reached from the degree of the reduction of the radiation quantity obtained by the first detection or detections of several times and then to recover the mixture solution when the frequency of the reciprocal liquid sending reaches the computed frequency. Further, it is also possible to detect radiation before recovery and to recover the mixture solution after whether the preset radiation quantity is reached is confirmed.

Further, it is also possible to detect radiation at given time intervals during reciprocal liquid sending and to recover the mixture solution when the preset radiation quantity is reached.

When the capacity of the biomolecule solution 121 used for reaction is small, a necessary quantity of the biomolecule solution 121 is sent in the state of being interposed by a gas or a solvent. When the biomolecule solution 121 is sent in the state of being interposed by a solvent, the reciprocal liquid sending range is adjusted by the quantity of a sent liquid so that only the biomolecule solution 121 may pass through the radioactivity labeling agent solidification section 25. When the biomolecule solution 121 is sent in the state of being interposed by a gas or a solvent, a sample loop not shown in the figure may be used.

EXAMPLE 15

Figures 20, 21:
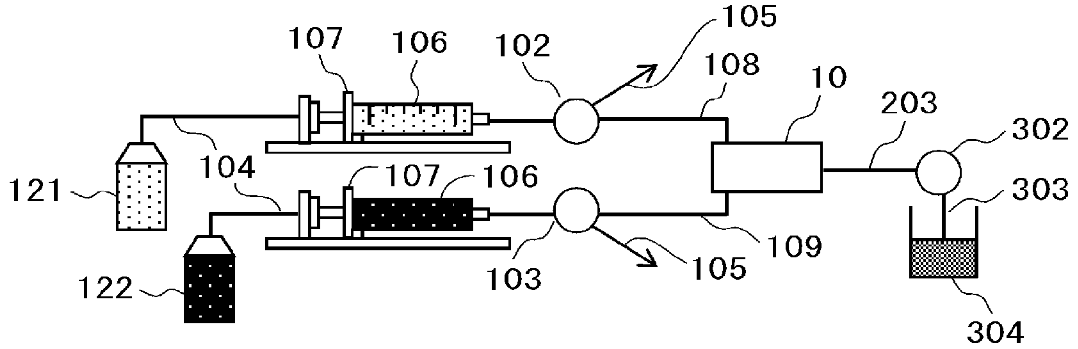
FIG. 20 is a table explaining an example of the relationship between the sizes and the capacities at sections of a flow channel structure formed in a reaction container main body (Example 15).
FIG. 21 is a view showing an example of a flow channel used for sending a sample liquid to a reaction container (Example 16).

In the present example, an example of the capacities of sections in a biomolecule radioactivity labeling reaction container 10 when a tiny amount of radioactivity labeling agent in the order of pg is handled is explained in reference to the table shown in FIG. 20. The table in FIG. 20 shows the sizes and the capacities of flow channel sections in the present example. A liquid sending structure in a reaction container main body 20 is the structure of Example 1 shown in FIGS. 3A and 4. In order to keep solution concentrations for handling a tiny amount of radioactivity labeling agent in the order of pg, solutions of low capacities of tens μL to hundreds μL are introduced into the reaction container main body 20.

In the present example, a biomolecule solution induction flow channel section 23 includes thirty-one flow channels having the width and the depth of 200 μm each and being formed at the intervals of 200 μm in the width direction. The actual capacity is 7 μL.

A radioactivity labeling agent solidification section 25 to introduce a radioactivity labeling agent solution 122 and remove a solvent and solidify it was formed so as to be somewhat deeper than the depth 200 μm of the biomolecule solution induction flow channel section 23 and the capacity of the funnel shape was 17 μL in the present example. When the capacity of the radioactivity labeling agent solution 122 to be introduced into the radioactivity labeling agent solidification section 25 is not less than 17 μL, the radioactivity labeling agent solution 122 is introduced in several batches or introduced by increasing the condensation of the solution and reducing the capacity to not more than 17 μL.

In the present example, a discharge side flow channel section 26 is a linear flow channel having the width and the depth of 500 μm each and the length of 13 mm and the capacity is 3 μL.

When a biomolecule solution 121 of not less than the capacity 27 μl, of a flow channel 21 is used, a necessary capacity is secured by the capacities of a mixed solution discharge section 27, a reservoir section 203, and a mixture solution recovery line 303 as well as the capacities of a biomolecule solution accumulation section 28*a*, a biomolecule solution supply section 22, and a biomolecule solution introduction section 108.

EXAMPLE 16

Here, an example of flow channels used for sending samples to a biomolecule radioactivity labeling reaction container 10 in a biomolecule radioactivity labeling reactor 1 (FIG. 1) is explained. The outline of liquid sending flow channels according to the present example is shown in FIG. 21.

The capacities of syringes 106 to send a biomolecule solution 121 and a radioactivity labeling agent solution 122 may be selected in accordance with the quantities of the sent solutions. In the present example, the capacities are set at 1 mL.

Further, the flow channel widths of solution sucking lines 104 may be selected in accordance with the capacities of the biomolecule solution 121 and the radioactivity labeling agent solution 122 to be sent. If a flow channel width reduces, however, a sucking time to a syringe 106 increases. In the present example, the flow channel widths are set at 0.5 mm.

Furthermore, the flow channel widths of solution wasting lines 105 may be selected in accordance with the capacities of the biomolecule solution 121 and the radioactivity labeling agent solution 122 to be sent. A narrow flow channel width is desirable for reducing a dead volume, but a wide flow channel width is desirable for increasing a waste liquid speed. In the present example, the flow channel widths are set at 1 mm.

The flow channel widths of a biomolecule solution introduction section 108 and a radioactivity labeling agent solution introduction section 109 may be selected in accordance with the capacities of the biomolecule solution 121 and the radioactivity labeling agent solution 122 to be sent. A narrow flow channel width is desirable for reducing a dead volume, but a wide flow channel width is desirable for increasing a liquid sending capability. In the present example, the flow channel widths are set at 0.5 mm.

The flow channel widths of a reservoir section 203 and a mixture solution recovery line 303 may be selected in accordance with the capacities of the biomolecule solution 121 and the radioactivity labeling agent solution 122 to be sent. A desirable flow channel width is not more than 1 mm in order to improve reaction efficiency. In the present example, the flow channel widths are set at 0.5 mm.

The flow channel lengths of the solution sucking lines 104, the solution wasting lines 105, the biomolecule solution introduction section 108, the radioactivity labeling agent solution introduction section 109, the reservoir section 203, and the product recovery line 303 may be any lengths as long as the lengths do not hinder operations. In the present example, they are set as follows. The flow channel length of the solution sucking lines 104 is set at 600 mm, the flow channel length of the solution wasting lines 105 is set at 600 mm, the flow channel length of the biomolecule solution introduction section 108 is set at 600 mm, the flow channel length of the radioactivity labeling agent solution introduction section 109 is set at 600 mm, the flow channel length of the reservoir section 203 is set at 120 mm, and the flow channel length of the product recovery line 303 is set at 120 mm.

It is desirable for a liquid sending switch valve 103 to have a small dead volume. To that end, in the present example, the dead volume of the liquid sending switch valve 103 is set at 3.4 μL.

EXAMPLE 17

In the present example, the result of applying a reaction container 10 having the sizes shown in Example 15 (FIG. 20) and liquid sending flow channels having the sizes shown in Example 16 (FIG. 21) to a biomolecule radioactivity labeling reactor 1 according to the present example and carrying out biomolecule radioactivity labeling reaction is shown. Here, in the present example, a neurotensin 0.3 mg/mL boric-acid buffer solution (pH 8.9) is used as a biomolecule solution 121 and a 50 MBq [18F]SFB diethyl ether solution is used as a radioactivity labeling agent solution 122.

Firstly, 50 μL of the 50 MBq [18F]SFB diethyl ether solution was sent to the reaction container 10 and a radioactivity labeling agent solidification section 25 in the biomolecule radioactivity labeling reactor 1 in five batches at a rate of 0.5 mL/min at room temperature, the reaction container 10 was heated to 50° C., and the diethyl ether was vaporized and removed. Successively, 50 μL of the neurotensin 0.3 mg/mL boric-acid buffer solution (pH 8.9) is reciprocally sent to the reaction container 10 in the biomolecule radioactivity labeling reactor 1 at a rate of 0.5 mL/min at room temperature. About one minute was required for one cycle including liquid sending, switching of a liquid sending switch valve 102, detecting radiation, and reverse liquid sending.

Figure 22:
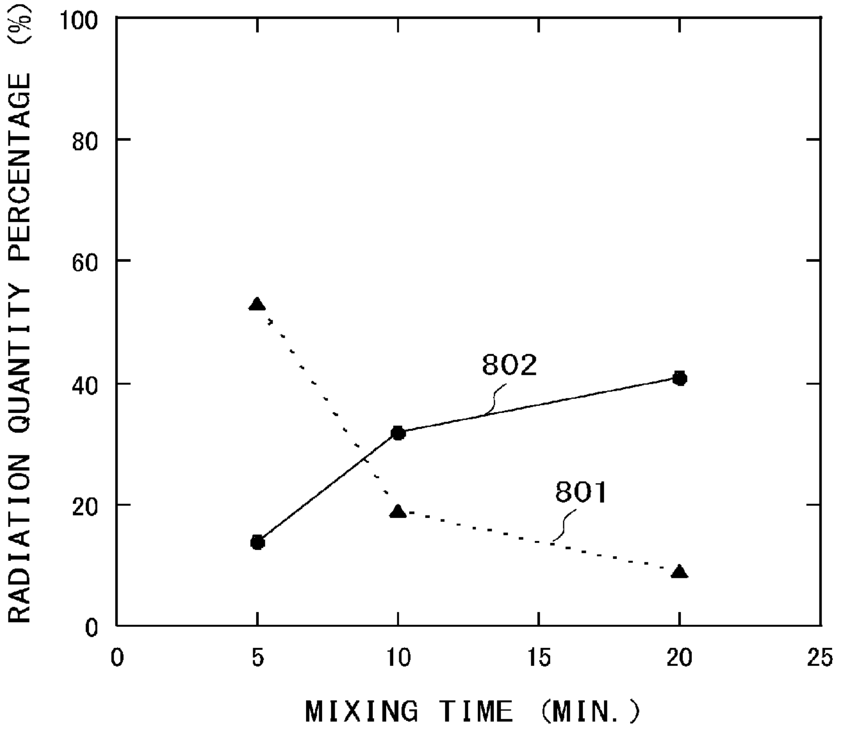
FIG. 22 is a graph showing an example of the result of radiochemical reaction in a biomolecule radioactivity labeling reactor (Example 17).

The result 801 obtained by monitoring the reaction in the present example with a radiation sensor shown in Example 5 (FIG. 8) is graphically shown in FIG. 22. The result 802 obtained by analyzing an obtained mixture solution 304 by HPLC with a radiation detector is also shown in FIG. 22. The vertical axis represents a radiation quantity ratio when the initial radiation quantity of the radioactivity labeling agent solidification section 25 is regarded as 100% and the horizontal axis represents a mixing time. As the result 802 shows, the yield of an [18F]SFB labeled neurotensin that was the objective substance improved as the mixing time in reciprocal liquid sending increased, but the improvement of the yield from 10 min to 20 min of mixing time was lower than the improvement of the yield from 5 min to 10 min. The result agreed with the decreasing trend of the radiation quantity of the radioactivity labeling agent solidification section 25 shown in the result 801.

From the result, it was found that a radioactivity labeling agent solidified in the radioactivity labeling agent solidification section 25 dissolved in a biomolecule solution through the reciprocal sending of the biomolecule solution and reacted with a biomolecule. Further, it was found that the moment of stopping the mixture by reciprocal liquid sending could be decided beforehand by monitoring the reduction of the radiation quantity of the radioactivity labeling agent solidification section 25.

When the labeling reaction of biomolecule neurotensin is performed by using [18F]SFB under the same reaction conditions as the present example, effective mixing time can be set by setting the operation so as to stop mixing when the radiation quantity of the radioactivity labeling agent solidification section 25 reaches 20% or lower of the initial value. Further, it is also possible to judge mixing time in conjunction with information on half-life of a nuclide in a labeled material.

Figure 23:
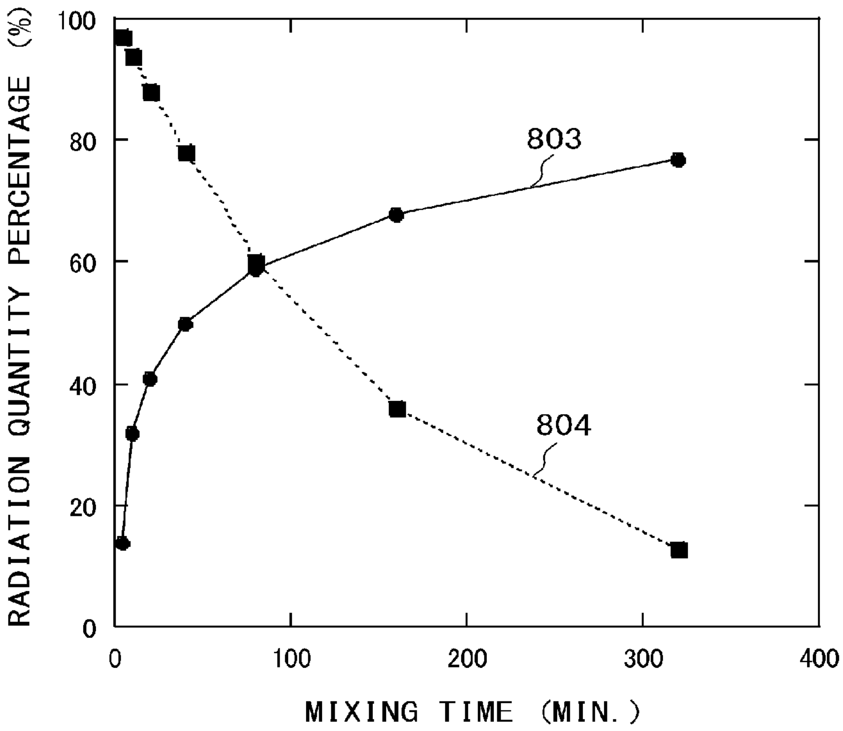
FIG. 23 is a graph showing an example of the relationship between the result of radiochemical reaction and the decay of the radioactivity of a labeling agent in a biomolecule radioactivity labeling reactor (Example 17).

The decay of the half-life of 18F is graphically shown as the result 804 in FIG. 23. The vertical axis represents a radiation quantity ratio when the initial radiation quantity of the radioactivity labeling agent solidification section 25 is regarded as 100% and the horizontal axis represents a mixing time. The yield of the [18F]SFB labeled neurotensin as the extension of the result 802 in FIG. 22 is shown by the curve of the result 803.

By considering the results 802 and 803 in combination, it is obvious that, even when reaction time is prolonged with the aim of improving the yield of the [18F]SFB labeled neurotensin, the radiation quantity of the obtained [18F]SFB labeled neurotensin decreases by decay when the mixing time elapses about 100 min. It is also possible to set the reaction so as to stop mixing when the mixing time reaches 100 min even though the radiation quantity of the radioactivity labeling agent solidification section 25 does not reach a set value.

EXAMPLE 18

Figure 24:
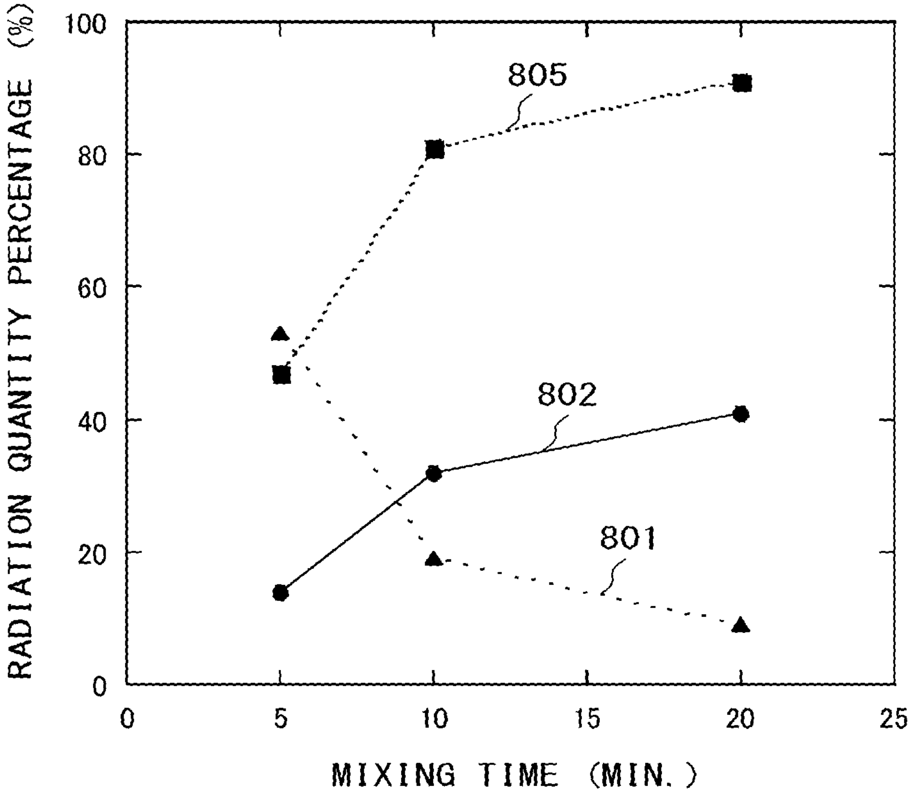
FIG. 24 is a graph showing an example of the result of radiochemical reaction in a biomolecule radioactivity labeling reactor (Example 18).

In the present example, the result obtained by monitoring operation similar to Example 17 with radiation sensors shown in Example 7 (FIG. 10) is graphically shown in FIG. 24. That is, radiation was monitored at two sites of a radioactivity labeling agent solidification section 25 and a mixture solution discharge section 27. The vertical axis of the graph represents a radiation quantity ratio when the initial radiation quantity of the radioactivity labeling agent solidification section 25 is regarded as 100% and the horizontal axis represents a mixing time.

In the same manner as Example 17, the monitoring result of the radioactivity labeling agent solidification section 25 is shown as the result 801, the result of analyzing an obtained mixture solution 304 by HPLC with a radiation detector is shown as the result 802, and the radiation monitoring result of the mixture solution discharge section 27 is shown as the result 805. The trend of the improvement of the yield of the [18F]SFB labeled neurotensin that was the objective substance shown in the result 802 agreed with the trend of the increase of the radiation quantity of the mixture solution discharge section 27 shown in the result 805.

From the results, it is obvious that the moment of stopping mixing by reciprocal liquid sending could be predicted by monitoring either the reduction of the radiation quantity of the radioactivity labeling agent solidification section 25 or the increase of the radiation quantity of the mixture solution discharge section 27.

Here, although explanations have been made on the basis of using a radioactivity labeling agent as a labeling agent in the examples, the present invention is not limited to a radioactivity labeling agent and a fluorescent labeling agent may also be used for example.

EXPLANATION OF REFERENCES

1 Biomolecule radioactivity labeling reactor
10 Biomolecule radioactivity labeling reaction container
20 Reaction container main body
21 Flow channel
22 Biomolecule solution supply section
22A Biomolecule solution supply nozzle
23 Biomolecule solution induction flow channel section
24 Radioactivity labeling agent solution supply section
24A Radioactivity labeling agent solution supply nozzle
25 Radioactivity labeling agent solidification section
25' Radioactivity labeling agent solidification section
26 Discharge side flow channel section
26' Discharge side flow channel section
27 Mixture solution discharge section
28*a* Biomolecule solution accumulation section
28*b* Radioactivity labeling agent solution accumulation section
29 Groove
30 Lid member
31 Discharge outlet port sections
40 Lid member
41 Outlet section
42 Gas discharge port
50 Adapter member
51 Inlet port section
52 Outlet port section
60 Adapter member
61 Inlet section
62 Outlet section
63 Biomolecule solution introduction port
64 Radioactivity labeling agent solution introduction port
65 Mixture solution discharge port
101 Liquid sending unit
102 Liquid sending switch valve 1
103 Liquid sending switch valve 2
104 Solution sucking line
105 Solution wasting line
106 Syringe
107 Syringe pump
108 Biomolecule solution introduction section
109 Radioactivity labeling agent solution introduction section
121 Biomolecule solution
122 Radioactivity labeling agent solution
131A Temperature control signal
131B Feedback signal
132A Radiation detection signal
132B, 132C Feedback signal
141A Control signal
141B Feedback signal
142, 143, 144, 145, 146 Data communication signal
201 Reaction container unit
202 Radiation sensor
203 Reservoir section
204 Radiation detector
205 Shielding section
206 Distance between detector and radioactivity labeling agent solidification section
207 Distance between detector and radioactivity labeling agent solidification section–distance in radioactivity labeling agent solidification section
208 Space section
301 Recovery unit
302 Recovery switch valve
303 Mixture solution recovery line
304 Mixture solution
401 Exhaust unit
402 Exhausting switch valve
403 Exhausting line
501 Temperature regulating unit
601 Radiation detection unit
701 Control unit

801 Detection result of radiation quantity of radioactivity labeling agent solidification section

802 Analysis result of [18F]SFB labeled neurotensin

803 Mixing time extension prediction of analysis result of [18F]SFB labeled neurotensin

804 Decay curve of [18F]SFB

805 Detection result of radiation quantity of mixed solution discharge section

The invention claimed is:

1. A biomolecule labeling reaction container to label a first chemical compound that is a biomolecule with a second chemical compound that is a radioactivity labeling agent, wherein the reaction container has a reaction container main body and a lid member formed oppositely on a top face side of the reaction container main body;

the reaction container has introduction sections of a solution of the first chemical compound and a solution of the second chemical compound and a recovery section of a labeled solution on a bottom face side of the reaction container main body;

a flow channel is formed on the top face of the reaction container main body;

a radioactivity labeling agent solidification section to remove a solvent in the solution of the second chemical compound and solidify the second chemical compound is formed at an intermediate section of the flow channel;

in the flow channel, a supply section of the solution of the first chemical compound, a solution induction flow channel section and a supply section of the solution of the second chemical compound are formed in order on the upstream side of the radioactivity labeling agent solidification section and a discharge section of the labeled solution is formed on the downstream side of the radioactivity labeling agent solidification section; and a first radiation sensor is positioned to detect radiation of the radioactivity labeling agent solidification section.

2. The biomolecule labeling reaction container according to claim 1, wherein a second radiation sensor is positioned to detect radiation in the vicinity of the discharge section of the labeled solution.

3. The biomolecule labeling reaction container according to claim 1, wherein an exhaust section to exhaust an evaporated solvent is formed at the lid member in the vicinity of both the ends of the radioactivity labeling agent solidification section.

4. The biomolecule labeling reaction container according to claim 1, wherein the radioactivity labeling agent solidification section includes a recess sagging from the top face of the reaction container main body in the thickness direction.

5. The biomolecule labeling reaction container according to claim 1, wherein the width and the depth of the flow channel formed on the top face of the reaction container main body are not more than 1 mm.

6. The biomolecule labeling reaction container according to claim 1, wherein the solution induction flow channel section includes a plurality of flow channels formed parallel to each other.

7. The biomolecule labeling reaction container according to claim 1, wherein the solution induction flow channel section includes a plurality of spaces having a given width and being interposed between two walls formed in parallel.

8. A reactor to label a first chemical compound that is a biomolecule with a second chemical compound that is a radioactivity labeling agent in a reaction container, having:

a reaction container unit including a reaction container, wherein a flow channel is formed on a top face of a reaction container main body; a radioactivity labeling agent solidification section to remove a solvent in the solution of the second chemical compound and solidify the second chemical compound is formed at an intermediate section of the flow channel; a supply section of a solution of the first chemical compound, a solution induction flow channel section and a supply section of a solution of the second chemical compound are formed in order on the upstream side of the radioactivity labeling agent solidification section; a discharge section of the labeled solution is formed on the downstream side of the radioactivity labeling agent solidification section; and a radiation sensor is positioned to detect radiation of the radioactivity labeling agent solidification section;

a liquid sending unit to supply the solution of the first chemical compound and the solution of the second chemical compound to the reaction container respectively and reciprocally send the solution of the first chemical compound to an upper part of the second chemical compound solidified at the radioactivity labeling agent solidification section;

a recovery unit to recover a labeled solution in the reaction container;

a radiation detection unit to measure a radiation quantity on the basis of a detection signal of the radiation sensor; and a control unit to control the reaction container unit, the liquid sending unit, the recovery unit, and the radiation detection unit;

wherein the control unit stops reciprocal liquid sending by the liquid sending unit on the basis of the radiation quantity of the radiation detection unit.

9. A reaction method of labeling a first chemical compound that is a biomolecule with a second chemical compound that is a radioactivity labeling agent by using a reaction container, wherein a flow channel is formed on a top face of a reaction container main body, a radioactivity labeling agent solidification section is formed at an intermediate section of the flow channel, a supply section of a solution of the first chemical compound, a solution induction flow channel section and a supply section of a solution of the second chemical compound are formed in order on the upstream side of the radioactivity labeling agent solidification section, a discharge section of the labeled solution is formed on the downstream side of the radioactivity labeling agent solidification section, and a radiation sensor is positioned to detect radiation of the radioactivity labeling agent solidification section, the method comprising the processes of:

introducing the solution of the second chemical compound that is the radioactivity labeling agent from a supply section of the second chemical compound into the radioactivity labeling agent solidification section, removing a solvent, and solidifying the second chemical compound;

introducing a solution of the first chemical compound that is the biomolecule from a supply section of the first chemical compound;

allowing a solution of the first chemical compound to pass reciprocally through an upper part of the solidified second chemical compound and labeling the first chemical compound with the second chemical compound;

detecting radiation of the solidified second chemical compound; and stopping reciprocal liquid sending when a detected radiation quantity reaches a preliminary set numerical value and recovering the labeled solution.

* * * * *